(12) United States Patent
Gao et al.

(10) Patent No.: US 12,064,311 B2
(45) Date of Patent: *Aug. 20, 2024

(54) VISUAL PRESENTATION OF GINGIVAL LINE GENERATED BASED ON 3D TOOTH MODEL

(71) Applicant: Align Technology, Inc., San Jose, CA (US)

(72) Inventors: Yun Gao, Cary, NC (US); Chao Shi, Morrisville, NC (US); Yingjie Li, Cary, NC (US); Andrey Bushev, Morrisville, NC (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/131,233

(22) Filed: Apr. 5, 2023

(65) Prior Publication Data
US 2023/0346513 A1    Nov. 2, 2023

Related U.S. Application Data

(63) Continuation of application No. 16/872,925, filed on May 12, 2020, now Pat. No. 11,642,195.

(Continued)

(51) Int. Cl.
*A61C 7/00*    (2006.01)
*A61B 34/10*    (2016.01)
(Continued)

(52) U.S. Cl.
CPC ............. *A61C 7/002* (2013.01); *A61B 34/10* (2016.02); *G06T 7/0012* (2013.01); *G06T 19/20* (2013.01); *A61B 2034/105* (2016.02); *G06T 2200/08* (2013.01); *G06T 2207/30036* (2013.01); *G06T 2210/41* (2013.01)

(58) Field of Classification Search
CPC ... A61C 7/002; A61B 34/10; A61B 2034/105; G06T 7/0012; G06T 19/20; G06T 2200/08; G06T 2207/30036; G06T 2210/41
See application file for complete search history.

(56) References Cited

U.S. PATENT DOCUMENTS 6,227,850 B1    5/2001  Chishti et al.
6,227,851 B1    5/2001  Chishti et al.
(Continued)

*Primary Examiner* — Michelle Chin
(74) *Attorney, Agent, or Firm* — Wilson Sonsini Goodrich & Rosati

(57) ABSTRACT

Systems and methods of simulating dental treatments are disclosed. A method may include capturing a first 2D image of a patient's face, including the patient's teeth, building a parametric 3D model of the patient's teeth and gingiva based on the first 2D image, developing a simulated outcome of a dental treatment of the patient's teeth by rendering the parametric 3D model with the patient's teeth in one or more positions and/or orientations corresponding to the treatment goals of the dental treatment plan, and rendering a second 2D image of the patient's face with gingiva and teeth according to a simulated outcome of the dental treatment plan. As noted herein, the dental treatment plan may include orthodontic and/or restorative elements. The simulated outcome may correspond to estimated outcomes and/or intended outcomes of the dental treatment plan.

18 Claims, 26 Drawing Sheets

Related U.S. Application Data

(60) Provisional application No. 62/847,780, filed on May 14, 2019.

(51) Int. Cl.
*G06T 7/00* (2017.01)
*G06T 19/20* (2011.01)

(56) References Cited

U.S. PATENT DOCUMENTS

| | | |
|---|---|---|
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,154,381 B2 | 10/2021 | Roschin et al. |
| 11,259,896 B2 | 3/2022 | Matov et al. |
| 11,357,598 B2 | 6/2022 | Cramer |
| 11,395,717 B2 | 7/2022 | Yuryev et al. |
| 11,432,908 B2 | 9/2022 | Kopelman et al. |
| 11,464,604 B2 | 10/2022 | Makarenkova et al. |
| 11,478,334 B2 | 10/2022 | Matov et al. |
| 11,484,389 B2 | 11/2022 | Sterental et al. |
| 11,521,732 B2 | 12/2022 | Levin et al. |
| 11,534,272 B2 | 12/2022 | Li et al. |
| 11,553,988 B2 | 1/2023 | Mednikov et al. |
| 11,633,268 B2 | 4/2023 | Moalem et al. |
| 11,642,195 B2 | 5/2023 | Gao et al. |
| 11,651,494 B2 | 5/2023 | Brown et al. |
| 11,654,001 B2 | 5/2023 | Roschin et al. |
| 11,707,344 B2 | 7/2023 | Roschin et al. |
| 11,810,271 B2 | 11/2023 | Shi et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0029068 A1* | 2/2004 | Sachdeva ............... G16H 50/50 433/24 |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2016/0163115 A1 | 6/2016 | Furst |
| 2016/0250006 A1 | 9/2016 | Fisker et al. |
| 2016/0310235 A1 | 10/2016 | Derakhshan et al. |
| 2017/0273760 A1 | 9/2017 | Morton et al. |
| 2018/0280118 A1 | 10/2018 | Cramer |
| 2019/0117337 A1* | 4/2019 | Tsai ........................ G06T 11/60 |
| 2019/0259219 A1* | 8/2019 | Lancelle ................ G06T 19/20 |
| 2019/0328487 A1 | 10/2019 | Levin et al. |
| 2019/0328488 A1 | 10/2019 | Levin et al. |

(56) References Cited

U.S. PATENT DOCUMENTS

2020/0155274 A1 5/2020 Pimenov et al.
2020/0297458 A1 9/2020 Roschin et al.
2020/0306011 A1 10/2020 Chekhonin et al.
2021/0134436 A1 5/2021 Meyer et al.

* cited by examiner

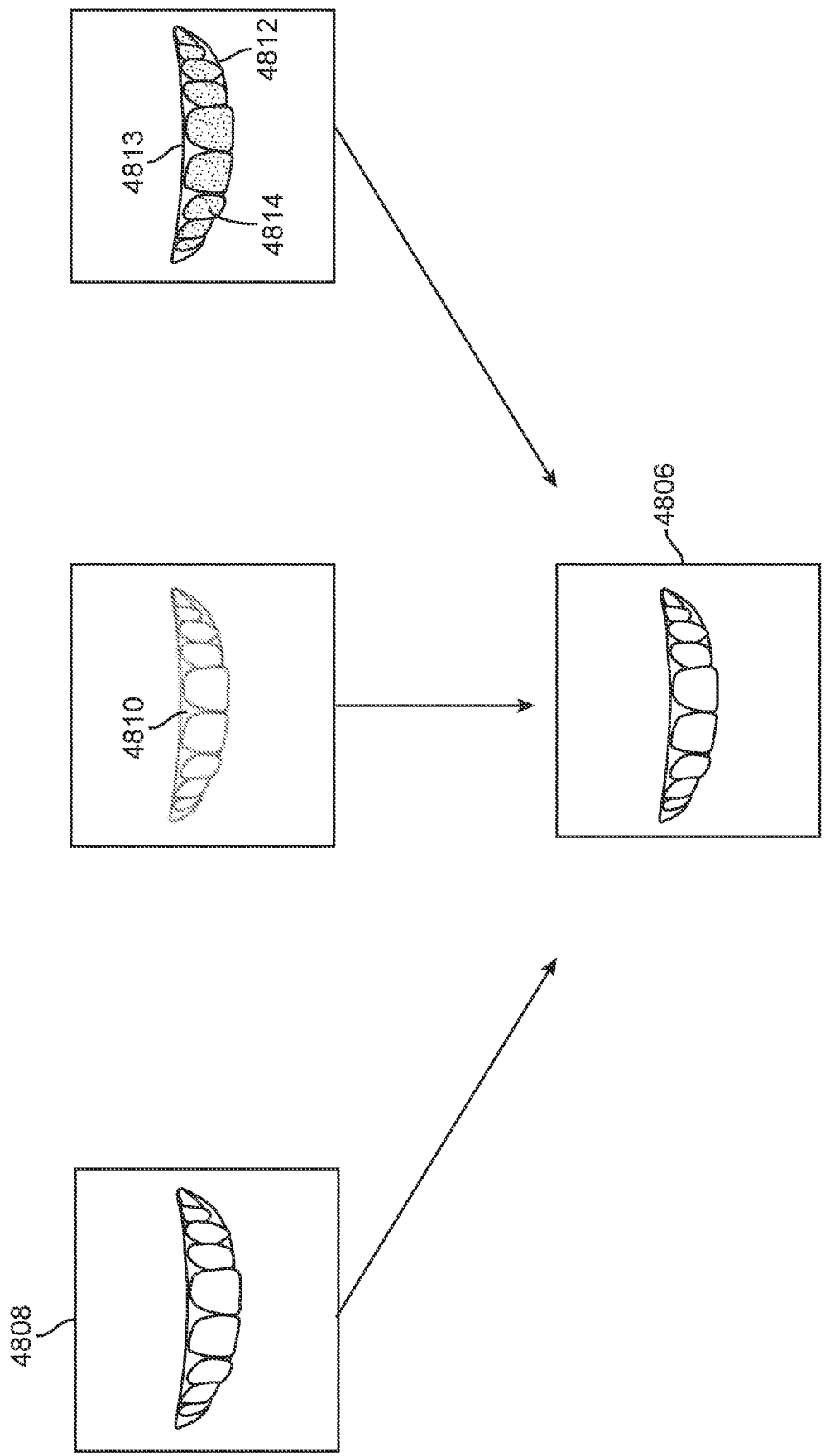

VISUAL PRESENTATION OF GINGIVAL LINE GENERATED BASED ON 3D TOOTH MODEL

CROSS-REFERENCE

This application is a continuation of U.S. application Ser. No. 16/872,925 filed May 12, 2020, now U.S. Pat. No. 11,642,195 issued May 9, 2023, which claims the benefit of U.S. Provisional Application No. 62/847,780, filed May 14, 2019, each of which are incorporated herein by reference.

TECHNICAL FIELD

The technical field relates to digital dental technologies, and more particularly to providing a simulated outcome of dental (e.g., orthodontic, restorative, etc.) treatment by evaluating a two-dimensional (2D) depiction of a patient's untreated teeth against parameters associated with model tooth arches.

BACKGROUND

Orthodontic treatment often includes addressing issues with malpositioned teeth and/or jaws and may include diagnosis, prevention, and/or correction of malocclusions. A person seeking orthodontic treatment may seek a treatment plan from an orthodontist, such as a professional who has undergone special training after graduating from dental school. Many orthodontic treatment plans include treatment with braces, brackets, wires, and/or polymeric appliances. A person seeking orthodontic treatment may have orthodontic appliances adjusted at various times by an orthodontic professional who designs and/or implements the orthodontic appliances.

Many people are referred for orthodontic treatment by dentists, other treatment professionals, or other people. For instance, many teenage patients or people with severe malocclusions may be referred for orthodontic treatment by their dentists or parents. However, many other people may not know whether or not they should receive orthodontic treatment. As an example, many individuals with mild malocclusions may not know whether or not orthodontic treatment is appropriate or desirable for them.

Additionally, many people may wish to visualize examples of their smiles without malpositioned teeth and/or jaws, e.g., after estimated and/or intended dental treatment(s), after insertion of implants or other devices, with configurations that would be appropriate for their face, age, heritage, and/or lifestyle, etc. While it may be desirable to provide people with the ability to visualize how their smiles and/or faces would look after possible treatment options, the computational burdens and/or costs of existing tools make it hard to do so. Existing tools also make it hard to visualize how dental treatment would meaningfully impact patients' lives.

SUMMARY

This disclosure generally relates to systems, methods, and/or computer-readable media related to simulating dental treatment of a patient's teeth, and particularly to providing a more photo-realistic rendering of a two-dimensional (2D) image of a patient that represents one or more simulated (e.g., estimated and/or intended) outcomes of a dental treatment plan. The implementations herein produce near accurate and realistic renderings of simulated outcomes of dental treatment and/or animations of three-dimensional (3D) models that could previously have not been generated, or generated only in a rudimentary fashion through manual photo editing tools. As noted herein, the implementations described use automated agents and/or rules to provide accurate and realistic renderings of simulated outcomes of dental (e.g., orthodontic, restorative, etc.) treatment and/or animations of 3D models that were previously not possible. The implementations herein allow people considering and/or undergoing orthodontic treatment the ability to visualize on a computer automatically generated simulated orthodontic treatment outcome simulations, and may inform a person's choices as to whether or not to seek orthodontic treatment in general and/or specific courses of orthodontic treatment. As noted herein, the disclosure also relates to systems and methods of accurately and realistically simulating 3D models of teeth in final orthodontic positions in a 2D image of person.

A computer-implemented method of simulating one or more simulated outcomes of dental treatment is disclosed. In some embodiments, the computer-implemented method of simulating orthodontic treatment may include capturing a first 2D image. In some embodiments, the first 2D image may include a representation of a patient's face and a patient's teeth. The method may include identifying one or more shapes associated with at least one of the patient's teeth. The method may also include building a parametric 3D model of the patient's teeth based on the first 2D image, using one or more case-specific parameters for the one or more shapes associated with the at least one of the patient's teeth. The method may also include simulating an outcome of a dental treatment plan for the patient's teeth to produce a simulated outcome of the dental treatment plan; and modifying the parametric 3D model to provide a modified 3D model representing the simulated outcome of the dental treatment plan. The method may also include rendering, using the modified 3D model, a second 2D image representing the patient's face, wherein the second 2D image represents the patient's teeth in accordance with the simulated outcome of the dental treatment plan.

In some embodiments, building the parametric 3D model includes finding edges of teeth and lips in the first 2D image, aligning a parametric tooth model to the edges of the teeth and lips in the first 2D image to determine the case-specific parameters, and storing the case-specific parameters of the parametric tooth model that align the parametric tooth model with the edges of the teeth, gingiva, and lips in the first 2D image.

In some embodiments, rendering the second 2D image includes accessing the parametric 3D model of the patient's teeth, projecting one or more teeth positions from the first 2D image onto the parametric 3D model, and mapping color data from the 2D image to corresponding locations on the parametric 3D model to generate textures for the parametric 3D model, and using the textures as part of the second 2D image of the patient's face.

In some embodiments, the predetermined position is based on an average position of a plurality of previous patients' teeth after dental treatment.

In some embodiments, the predetermined position is based on an average position of a plurality of previous patients' teeth before dental treatment.

In some embodiments, the computer-implemented method may include finding edges of teeth and lips in the first 2D image, and aligning the parametric 3D tooth model to the edges of the teeth, gingiva, and lips in the first 2D image.

In some embodiments, the first 2D image may include a profile image representing a profile of the patient's face.

In some embodiments, the simulated outcome of the dental treatment plan may include an estimated outcome of the dental treatment plan.

In some embodiments, the simulated outcome of the dental treatment plan may include an intended outcome of the dental treatment plan.

In some embodiments, the dental treatment plan may include an orthodontic treatment plan, a restorative treatment plan, or some combination thereof.

In some embodiments, capturing the first 2D image may include instructing a mobile phone or a camera to image the patient's face, or gathering the first 2D image from a storage device or a networked system.

In some embodiments, building the parametric 3D model of the patient's teeth based on the 2D image, using one or more case-specific parameters for the one or more shapes associated with the at least one of the patient's teeth may include coarsely aligning teeth represented in the 3D parametric model to the patient's teeth represented in the 2D image, and executing an expectation step to determine a probability that a projection of a silhouette of the 3D parametric model matches one or more edges of the 2D image a first time.

In some embodiments, building the parametric 3D model of the patient's teeth based on the 2D image, using one or more case-specific parameters for the one or more shapes associated with the at least one of the patient's teeth may include executing a maximization step using a small angle approximation to linearize the rigid transformation of the teeth in the 3D model, and executing the expectation step to determine a probability that a projection of a silhouette of the 3D parametric model matches the edges of the 2D image a second time.

In some embodiments, the computer-implemented method may include iterating through the expectation and maximization steps a first plurality of times to with a first subset of parameters, and after iterating through the expectation and maximization steps the first plurality of times with the first subset of parameters of the 3D parametric model, iterating though the expectation and maximization steps the second plurality of times with the first and second subset of parameters.

In some embodiments, the computer-implement method may include capturing a first 2D image of a patient's face, including their teeth. The method may include building a parametric 3D model of the patient's teeth based on the 2D image, the parametric 3D model including case-specific parameters for the shape of at least one of the patient's teeth. The method may also include simulating an estimated (e.g., an estimated final) and/or intended (e.g., an intended final) orthodontic position of the patient's teeth by gathering information about one or more model tooth arches that represent smiles without malpositioned teeth and/or jaws, and by rendering the 3D model with the patient's teeth in a predetermined position (e.g., one corresponding to positions of teeth in the model arches) and rendering a second 2D image of the patient's face with teeth in an estimated orthodontic position.

In some embodiments, building a parametric 3D model includes finding edges of teeth and lips in the first 2D image, aligning a parametric tooth model to the edges of the teeth and lips in the first 2D image to determine the case-specific parameters, and storing the case-specific parameters of the parametric tooth model that align the parametric tooth model with the edges of the teeth, gingiva, and lips in the first 2D image.

In some embodiments, rendering the second 2D image includes rendering the parametric model of the patient's according to the position of the teeth in the first 2D image, projecting the 2D image onto the rendered parametric model of the patient's according to the position of the teeth in the first 2D image, and mapping the color data from the 2D image to corresponding locations on the 3D model to generate textures for the 3D model, and rendering the second 2D image of the patient's face with teeth in the estimated orthodontic position with the generated textures.

In some embodiments, rendering the second 2D image further includes applying simulated treatments or viewing customizations to the second 2D image.

In some embodiments, the simulated treatments or viewing customizations may include one or more of changing an edge of the gingiva, replacing a tooth, adjusting a jaw position, or adjusting the color data.

In some embodiments, the predetermined position is based on a combination of (e.g., an average) positions of a plurality of previous patients' teeth after orthodontic treatment and/or without misaligned teeth or jaws.

In some embodiments, the predetermined position is based on a combination of (e.g., an average) positions of a plurality of previous patients' teeth before orthodontic treatment.

In some embodiments, the method may include finding edges of teeth and lips in the first 2D image, and aligning the parametric tooth model to the edges of the teeth, gingiva, and lips in the first 2D image.

In some embodiments, the first 2D image comprises a profile image.

A computer-implemented method of building a 3D model of teeth from a 2D image is disclosed. The method may include capturing a 2D image of a patient's face, including their teeth, determining edges of teeth and gingiva within the first 2D image, fitting the teeth in a 3D parametric model of teeth to the edges of the teeth and gingiva within the first 2D image, the 3D parametric model including case-specific parameters for the shape of the patient's teeth, determining the value of the case-specific parameters of the 3D parametric model based on the fitting.

In some embodiments, the fitting of the teeth in the 3D parametric model of teeth to the edges of the teeth and gingiva within the first 2D image comprises: coarsely aligning the teeth in the 3D parametric model to the teeth in the 2D image, and executing an expectation step to determine a probability that a projection of a silhouette of the 3D parametric model matches the edges of the 2D image.

In some embodiments, the fitting of the teeth in the 3D parametric model of teeth to the edges of the teeth and gingiva within the first 2D image further comprises: executing a maximization step using a small angle approximation to linearize the rigid transformation of the teeth in the model, and executing the expectation step to determine a probability that a projection of a silhouette of the 3D parametric model matches the edges of the 2D image again.

In some embodiments, a computer-implemented method further comprises iterating through the expectation and maximization steps a first plurality of times with a first subset of parameters; and after iterating through the expectation and maximization steps the first plurality of times with the first subset of parameters of the 3D parametric model, iterating through the expectation and maximization steps the second plurality of times with the first and second subset of parameters.

In some embodiments, the first plurality of times is the same as the second plurality of times.

In some embodiments, the first subset of case-specific parameters of the 3D parametric model is one or more of a scale factor, tooth location, and orientation.

In some embodiments, the second subset of parameters of the 3D parametric model are one or more of a tooth shape and tooth location and orientation.

A computer-implemented method of providing a simulated outcome of orthodontic treatment is disclosed. The method may include building a 3D parametric model of an arch, the 3D parametric model comprising generic parameters for tooth shape, tooth position, and tooth orientation, capturing a 2D image of a patient, constructing a case-specific 3D parametric model of the patient's teeth from the 2D image, determining the case-specific parameters of the constructed parametric model, rendering the 3D parametric model of the patient's teeth in an estimated and/or intended final position (e.g., without misaligned teeth and/or jaws), and inserting the rendered 3D model into a 2D image of the patient.

In some embodiments, the constructing of a 3D parametric model of the patient's teeth from the 2D image includes: finding edges of teeth, gingiva, and lips in the first 2D image, and aligning the 3D model parametric to the edges of the teeth, gingiva, and lips in the first 2D image.

In some embodiments, the method further comprises applying textures to the rendered 3D parametric model of the patient's teeth in an estimated and/or intended final position (e.g., without misaligned teeth and/or jaws), wherein the textures are derived from the 2D image of the patient.

In some embodiments, the textures are derived from the 2D image of the patient by: projecting the 2D image onto the rendered parametric model of the patient's according to the position of the teeth in the first 2D image, and mapping the color data from the 2D image to corresponding locations on the 3D model to derive the textures for the 3D model.

In some embodiments, the rendering of the 3D parametric model of the patient's teeth in the estimated and/or intended final position comprises: generating a mean shape of teeth based on the 3D parametric model, adjusting the shape of the teeth in the 3D parametric model based on case-specific tooth shape parameters, positioning the teeth in a mean tooth location and orientation based on a mean location and orientation parameter such that the teeth have a case specific shape and a mean location and orientation, and scaling the arch based on a case-specific arch scaling parameter.

A non-transitory computer readable medium includes instruction that when executed by a processor cause the processor to perform any of the methods described herein.

A system is disclosed. The system may include a photo parameterization engine configured to generate a 3D parametric arch model from a 2D image of a patient's face and teeth, the parametric 3D model including case-specific parameters for the shape of at least one of the patient's teeth and a parametric treatment prediction engine configured to identify an estimated and/or intended outcome of orthodontic treatment of a patient based on the 3D parametric arch model and historic models of a plurality of patients and/or idealized tooth arch models.

In some embodiments, the system includes a treatment projection rendering engine configured to render the 3D parametric arch model.

In some embodiments, the photo parameterization engine, the parametric treatment prediction engine, and the treatment projection rendering engine are together configured to perform the methods described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 24 depicts a process of rendering a realistic composite image of patient's face and a model of a patient's teeth, in accordance with one or more embodiments herein.

DETAILED DESCRIPTION

Figure 1:
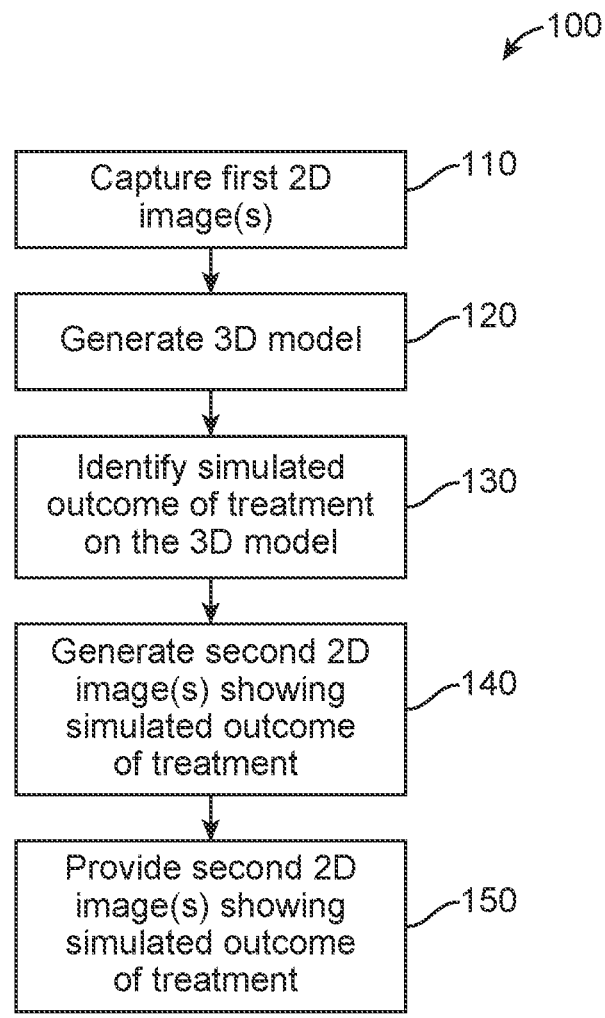
FIG. 1 illustrates a method of providing an estimated outcome of orthodontic treatment, in accordance with one or more embodiments herein.

The implementations discussed herein provide tools, such as automated agents, to visualize the effect of correcting malpositioned teeth/jaws, malocclusion, etc., without the computational burden(s) and/or expense(s) of scanning a patient's dentition or impressions of the dentition, and to calculate final positions of a treatment plan on a patient's dentition, etc. As discussed in detail herein, these techniques may involve obtaining a two-dimensional (2D) representation (such as an image) of a patient's dentition, obtaining one or more parameters to represent attributes of the patient's dentition in the 2D representation, and using the one or more parameters to compare the attributes of the patient's dentition with attributes of model arches, such as those of historical cases and/or those representing idealized arch forms. The techniques herein may provide a basis to simulate a simulated outcome of a dental treatment plan.

A "simulated outcome of a dental treatment plan," as used herein, may include an estimated and/or intended outcome of the dental treatment plan, such as after implementation of one or more dental procedures, such as orthodontic procedures, restorative procedures, etc. An "estimated outcome of a dental treatment plan," as used herein, may include an estimate of a state of a patient's dentition after dental procedures. An estimated outcome of a dental treatment plan, as used herein, may, in some instances, be different from an "actual outcome of a dental treatment plan," which may represent the state of a patient's dentition after implementation of the dental treatment plan. Estimated and actual outcomes of a dental treatment plan, as used herein, may, in various instances, be different from an "intended outcome of a dental treatment plan," which may represent the intended state of a patient's dentition after implementation of a dental treatment plan. It is further noted that an "estimated outcome of an orthodontic treatment plan" may include an estimate of a state of a patient's dentition after correction of any malpositioned teeth/jaws, malocclusion, etc., the patient suffers from. In some implementations, an estimated outcome of an orthodontic treatment plan includes the estimated state of the patient's dentition if the patient's dentition has been changed to have a model and/or ideal arch form, as reflected according to one or more databases of historical cases and/or idealized arch forms. An "actual outcome of an orthodontic treatment plan" may represent the state of a patient's dentition after implementation of the orthodontic treatment plan; an "intended outcome of an orthodontic treatment plan" may represent an intended state of a patient's dentition after implementation of an orthodontic treatment plan.

A better understanding of the features and advantages of the present disclosure will be obtained by reference to the following detailed description that sets forth illustrative embodiments, in which the principles of embodiments of the present disclosure are utilized, and the accompanying drawings.

FIG. 1 illustrates an example of a method 100 of providing an estimated and/or intended outcome of a dental treatment plan, in accordance with one or more embodiments herein. The method 100 may be executed by any of the systems disclosed herein. It is noted that various examples may include more or fewer blocks than those depicted in FIG. 1.

At block 110, one or more two-dimensional (2D or 2-D) image(s) of a patient are captured. In some embodiments, the 2D image(s) depict the mouth of the patient and include one or more images of the face, head, neck, shoulders, torso, or the entire patient. The 2D image(s) of the patient may include an image of the patient with the patient's mouth in one or more positions; for example, the patient's mouth may be a smiling position, such as a social smiling position, a repose position with relaxed muscles and lips slightly parted, or anterior retracted open bite or closed bite positions.

In some embodiments, the image of the patient is obtained with an image capture device. An "image capture device" (i.e., "image capture system") as used herein, may include any system capable of capturing an image. Examples of image captures devices include a camera, smartphone, digital imaging device, a component of a computer system configured to capture images, etc. The image may be captured with a lens at a predetermined focal length and at a distance from the patient. The image may be captured remotely and then received for processing. In some implementations, the image of the patient is obtained from a computer-storage device, a network location, a social media account, etc. The image may be a series of images or video captured from one or more perspectives. For example, the images may include one or more of a frontal facial image and a profile image, including one or more three-quarter profile images and full profile images.

At block 120, a three-dimensional (3D or 3-D) model of the patient's teeth is generated based on the 2D image of the patient. As discussed in more detail with respect to FIG. 6 and elsewhere herein, generating a 3D model may include identifying the patient's teeth. Generating a 3D model may further include identifying a patient's gums, lips, and/or mouth opening, forming a parametric model for each identified tooth, and combining the parametric teeth models into one or more (e.g., two, three, etc.) parametric arch models. The parametric models of the patient's teeth and arch may be based on or in reference to mean parametric tooth and arch models, as discussed further herein.

A "parametric model of a patient's teeth" (e.g., a "parametric model of a patient's dentition") as used herein, may include a model of a patient's dentition (e.g., a statistical model) characterized by a probability distribution with a finite number of parameters. A parametric model of a patient's dentition may include a parametric model of the patient's teeth and/or arch. A parametric model may comprise a model representing objects in various dimensions, and may include a parametric 2D model, a parametric 3D model, etc. Use of a parametric model of a patient's dentition to model the patient's teeth may reduce the memory and computational demands when manipulating, comparing, or otherwise using digital models, as descried herein and simplify comparisons between different models. In some implementations, a parametric model of a tooth can be expressed as:

$$S_\tau^C + \Sigma_i^{|B\tau|} a_\tau^i B_\tau^i \qquad \text{eq. (1)},$$

where $S_\tau^C$ is a mean tooth shape, a generic parameter. Each tooth (for example, tooth number 6, the upper right canine in the universal tooth numbering system, has its own mean tooth shape) calculated from thousands of teeth with same tooth number, as discussed herein. The symbol $\tau$ may represent the index for each tooth, which may be based on the universal tooth numbering system or another numbering system, $B_\tau^i$ may be the principal components of the shape of each tooth, also a generic parameter, and $a_\tau^i$ may be the coefficients for the principal components of the shape of the teeth, a case-specific parameter. Accordingly, eq. (1) can be used to express a parametric model of each of a specific patient's teeth based on each tooth's particular shape relative to a mean tooth shape for that tooth (for example, a left lower incisor, right upper canine, etc.).

A parametric model of a patient's dentition can be expressed as:

$$Z_\tau = \Phi T T_\tau T_\tau^C (S_\tau^C + \Sigma_i^{|B\tau|} a_\tau^i B_\tau^i) \qquad \text{eq. (2)},$$

where $S_\tau^C + \Sigma_i^{|B\tau|} a_\tau^i B_\tau^i$ is as discussed above with reference to eq. (1); $T_\tau^C$ is the mean tooth position, a generic parameter; $T_\tau$ is the deviation of the position of a patient's tooth from the corresponding mean tooth position, a case-specific parameter; and $\Phi$ is an arch scaling factor that scales the parametric, unit-less, values to real world values, also a case-specific parameter. T is the global perspective of the arch from a viewpoint and is a case-specific parameter and in some embodiments, is only used when matching to a 2D image, because arch scans typically do not have a perspective, whereas a 2D image, such as a camera does.

Figure 2:
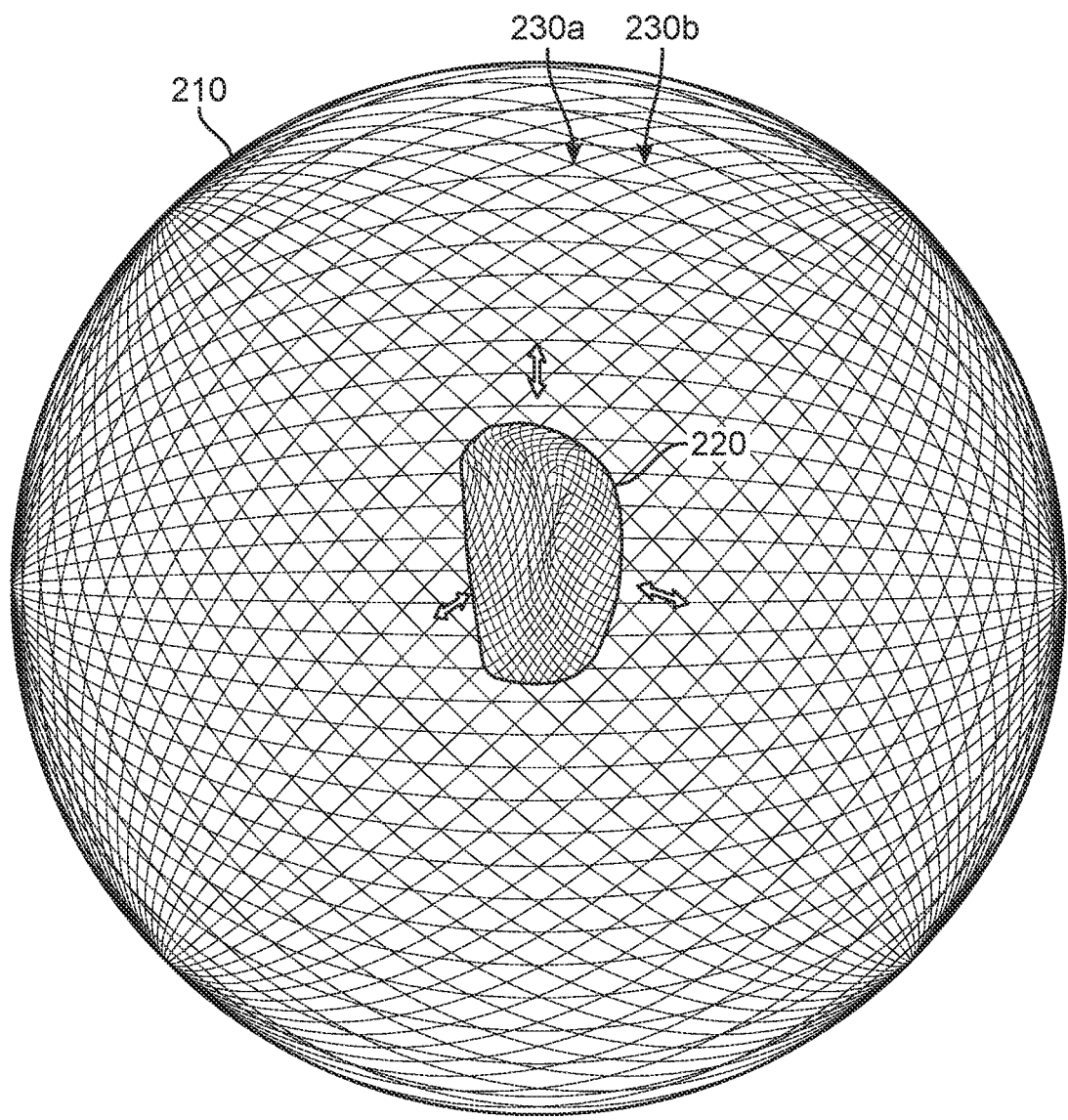
FIG. 2 illustrates a parametric tooth model, in accordance with one or more embodiments herein.
Figure 3A:
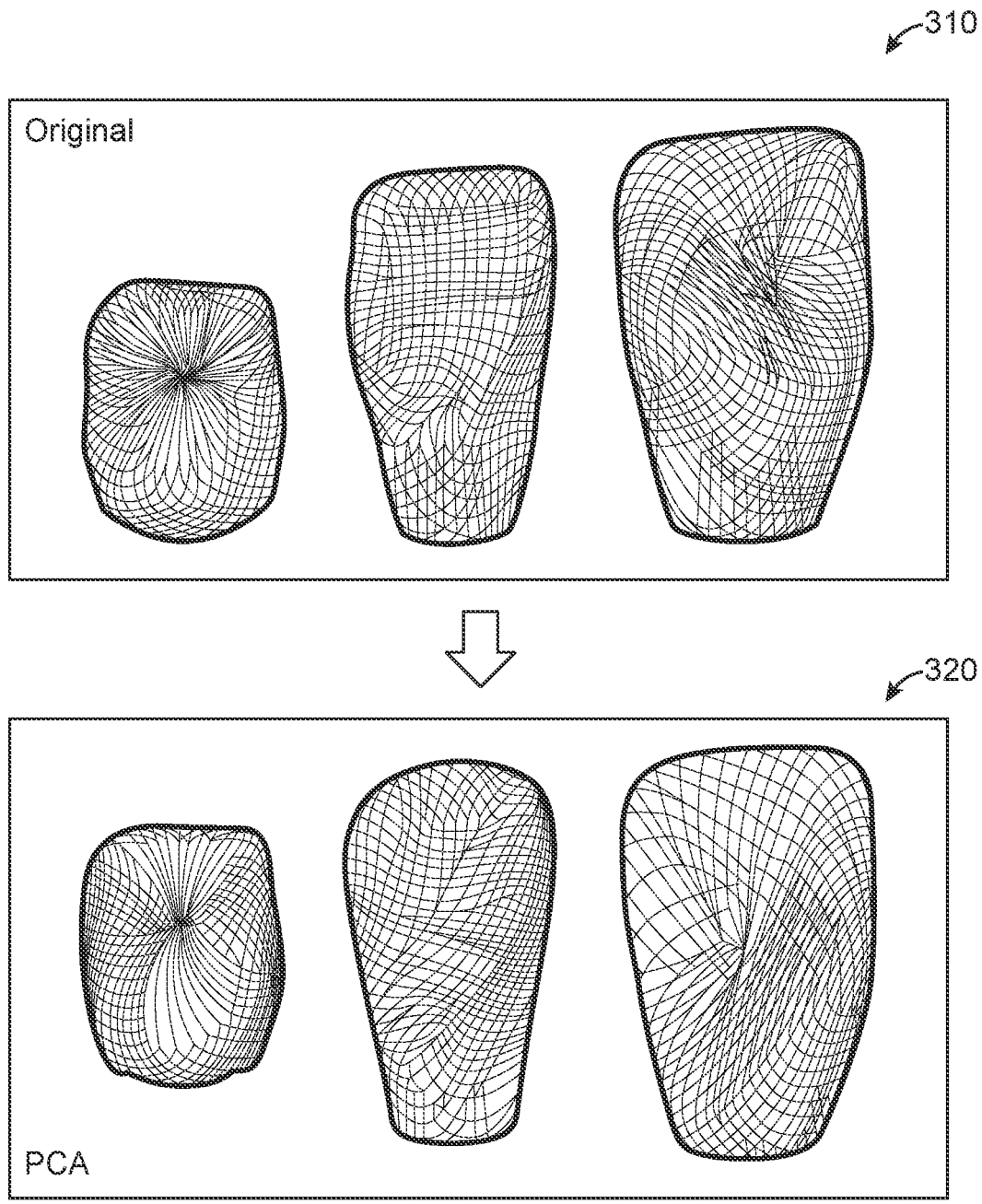
FIG. 3A illustrates an example of how well a parametric tooth model matches an original 3D model, in accordance with one or more embodiments herein.

To generate a parametric 3D model of a patient's tooth from a 3D tooth model derived from an image of a patient's tooth or from another method known in the art, the tooth may be modeled based on displacement of the scanned tooth surface from a fixed shape, such as a fixed sphere. To illustrate this point, reference is made to FIG. 2, illustrating a parametric tooth model, in accordance with one or more embodiments herein. In the example of FIG. 2, a sphere 210 having a plurality of vertices in fixed or known locations and orientations is shown. A tooth 220 may be placed or otherwise modeled at the center of the sphere 210. In some embodiments, the center of volume of the tooth 220, the scanned portion of the tooth 220, or the crown of the tooth 220, may be aligned with the center of the sphere 210. Then each vertex 230a, 230b of the sphere 210 may be mapped to a location on the surface of the tooth model. In some embodiments, the mapping may be represented by an n*3 matrix, where n represents the number of points on the sphere, such as 2500, and then for each point, the x, y, and z location is recorded. In some embodiments, the matrix stores the difference between a location on a mean tooth with the corresponding position on the model of the actual. In this way, each tooth is represented by the same 2500 points, and differences between the teeth are easily compared with each other. The difference may be represented using PCA components as $\Sigma_i^{|B\tau|} a_\tau^i B_\tau^i$, wherein each specific case eventually has a unique set of $a_\tau^i$, since $B_\tau^i$ is generic for all cases. To illustrate this point, reference is made to FIG. 3A, showing an example of how well parametric models 320 of the teeth match the original 3D models 310. The parameters of a particular tooth may be stored in a datastore, such as a database and may be represented by $a_\tau^i$.

A parametric model of a patient's arch may involve parameterizing the location and orientation of each tooth in an arch and the scale of the arch. The case-specific parameters for a particular tooth may be stored in a matrix or other datastore, as represented by eq. (3):

$$T_\tau = \begin{bmatrix} \xi_{00} & \xi_{01} & \xi_{02} & \Delta_{\tau,x} \\ \xi_{10} & \xi_{11} & \xi_{12} & \Delta_{\tau,y} \\ \xi_{20} & \xi_{21} & \xi_{22} & \Delta_{\tau,z} \\ 0 & 0 & 0 & 1 \end{bmatrix}; \qquad \text{eq. (3)}$$

where $\xi_{ij}$ are the rotational components that define the orientation of the tooth with respect to the arch and may be a function of $\alpha_\tau$, $\beta_\tau$, $\gamma_\tau$, the 3 rotation angles of the tooth. $\Delta_{\tau,x}$, $\Delta_{\tau,y}$, $\Delta_{\tau,y}$, and $\Delta_{\tau,z}$ are the translation of the center point of the tooth with respect to the arch origin. The rotation may be based on the orientation of orthogonal axis of each tooth, for example, the long axis, the buccal-lingual axis, and the mesial-distal axis with respect to a fixed reference or with respect to a mean rotation. In some embodiments one or more of these components may be represented as deviations or changes relative to a mean arch, discussed herein.

Similarly, the scaling factor, $\Phi$ is applied to the teeth and the arch locations of the teeth to scale the arch from a generic or unit-less representation to a real world scale that represents the actual size and location of the teeth in the arch. In some embodiments, scaling may be between projected 3D units, for example, millimeter, to images size, for example, pixels.

As discussed above, and elsewhere herein, the parametric models of the arch, including the teeth, may be represented based on a mean arch model, including the teeth. The mean arch model may be determined based on an average of a large dataset of patient arch scans. In some embodiments, the mean arch model may be based on a large dataset of parameterized arches.

Figure 3B:
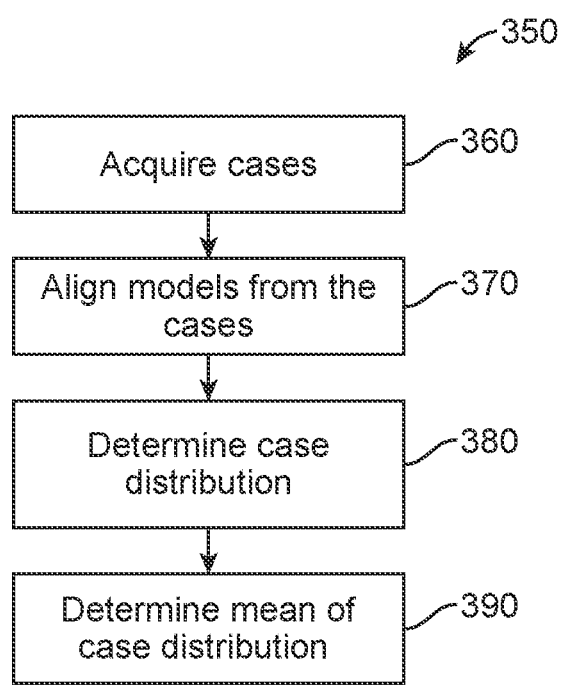
FIG. 3B illustrates a method of determining generic parameters from historic and/or idealized cases, in accordance with one or more embodiments herein.

For example, a mean arch may be built from a set of previously scanned and/or segmented arches. FIG. 3B depicts an example of a method 350 of determining a mean arch model and is discussed in detail further herein.

Figure 5:
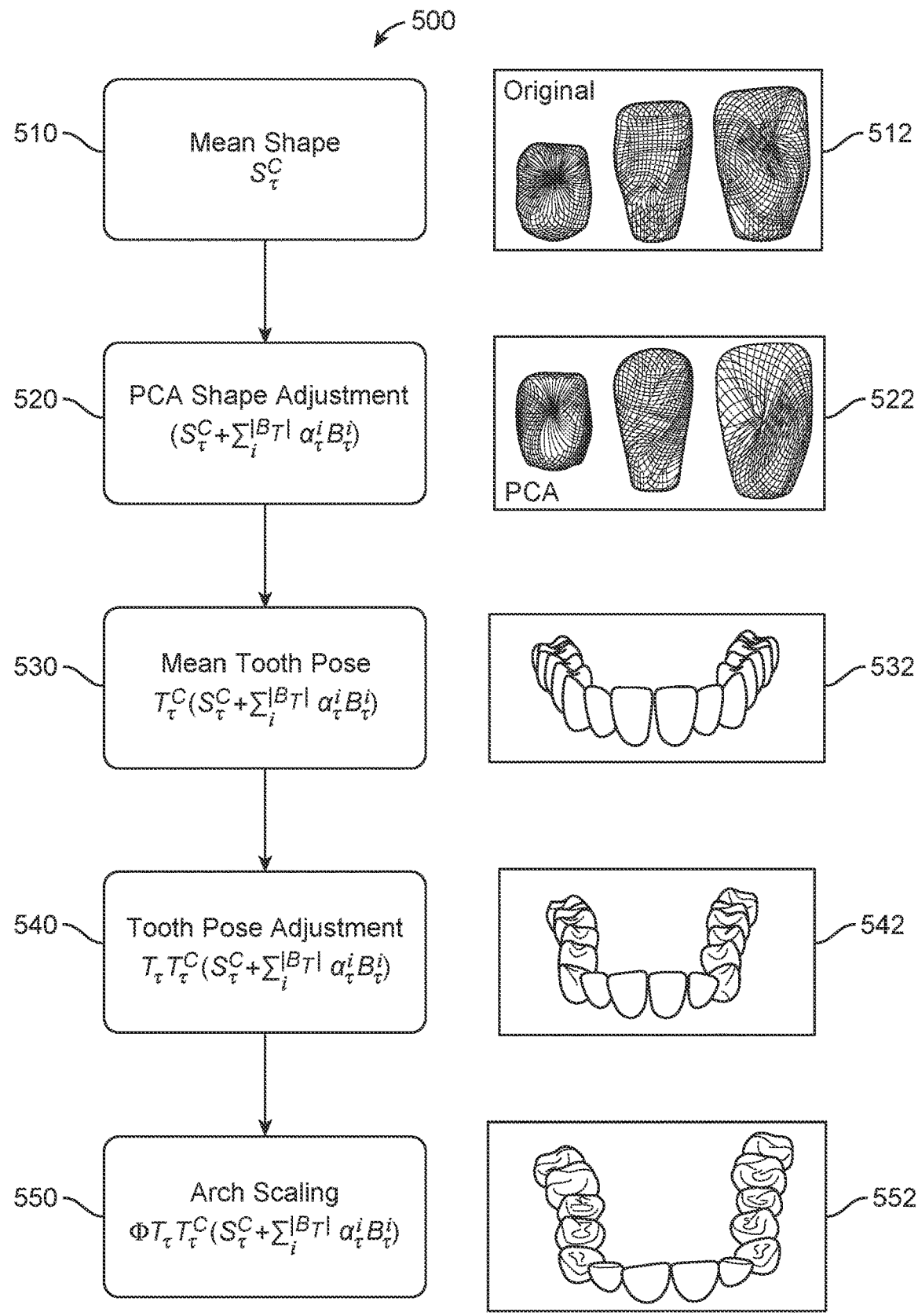
FIG. 5 depicts a method of generating a parametric model of a patient's teeth, and converting the parametric model into a 3D model of a dental arch, in accordance with one or more embodiments herein.

In some implementations, a parametric model of an arch may be converted into a 3D model of the arch. FIG. 5 depicts a method 500 of converting a parametric model of one or more teeth into a 3D model of a dental arch, according to some implementations, and is discussed in detail further herein.

Returning to FIG. 1, at block 130, an estimated and/or intended outcome of a dental treatment plan on the 3D model is identified to obtain an estimated and/or intended outcome of the orthodontic treatment plan. The estimated and/or intended outcome of a dental treatment plan may be based on a parametric model of the patient's teeth at positions indicated based on a predetermined arch model, as discussed with respect to FIGS. 9-11. In some embodiments, a predetermined arch model may be based on a mean arch model may be based on a historic mean of collected arch scans or other arch models from patients. In some embodiments, the predetermined arch model may be an idealized model, for example, based on a clinically ideal arch or an arch model wherein tooth positions and/or orientations are determined in advance, such as based on one or more of their aesthetic and clinical properties, such as proper occlusion. In some embodiments, an estimated and/or intended outcome of the dental treatment plan may correspond to an intended final position (or estimate thereof) of the patient's teeth after implementation of the treatment plan. In some embodiments, the estimated and/or intended outcome of dental treatment may correspond to estimates of final and intermediate positions during the course of the treatment plan. As noted herein, the dental treatment plan may comprise an orthodontic treatment plan, a restorative treatment plan, some combination thereof, etc.

At block 140, second 2D image(s) are generated showing the estimated and/or intended outcome of orthodontic treatment. The image(s) may be a 2D facial image of the patient with teeth aligned according the estimated and/or intended outcome of the dental treatment plan as discussed herein. In some embodiments, the image may include an estimated and/or projected texture of the patient's teeth, for example as discussed below, with respect to FIG. 9 and elsewhere herein. A "projected texture" or "estimated texture" of a patient's teeth, as used herein, may include a projection/estimation of texture of teeth and may include the feel, appearance, consistency, and/or other attributes of the surface of the teeth. At block 150, the second 2D image(s) generated at block 140 are provided to a user. For example, the image may be rendered for viewing by a patient or dental professional. In some embodiments, the second 2D image may be loaded into memory or retrieved from memory.

Turning to FIG. 3B, FIG. 3B illustrates a method of determining generic parameters from historic and/or idealized cases, in accordance with one or more embodiments herein. At block 360, historic and/or idealized cases are acquired. The historic and/or idealized cases may be retrieved from a datastore. The historic and/or idealized cases may include cases representing previously scanned and segmented arch models. In some implementations, the historic and/or idealized cases may represent arch models of treated patients (e.g., of patients who in the past have undergone treatment) and/or idealized arch models representing intended outcomes of various forms of orthodontic treatment. In various implementations, the historic and/or idealized cases may represent arch models with idealized arch forms. In some implementations, the historic and/or idealized cases may include regions where model arches have teeth that correspond to a location of an implant to be inserted into the arch of a patient.

Figure 4:
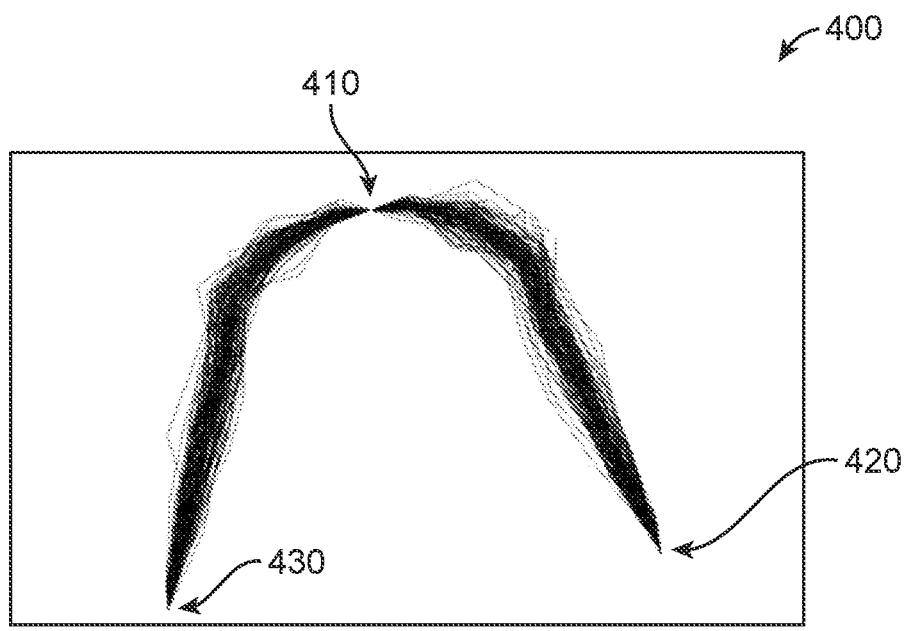
FIG. 4 illustrates the alignment of past cases for use in determining parameters of a parametric model, in accordance with one or more embodiments herein.

At block 370 the historic and/or idealized cases are aligned. In some implementations, each arch of the historical and/or idealized cases is aligned at a plurality of locations. As an example, each arch of the historical and/or idealized cases may be aligned at the following three locations: between the central incisors and at each distal end of the left and right side of each arch. For example, FIG. 4 shows a set of arches 400 aligned at location between the central incisors 410, at the left distal end of the arch 430, and the right distal end of the arch 420. It is noted the historic and/or idealized cases may be aligned at a variety of locations and a variety of numbers of locations without departing from the scope and substance of the inventive concepts described herein.

Returning to FIG. 3B, determining a mean arch model and determining arch model distributions may include performing sub operations at block 370. For example, each arch is averaged to determine $T_\tau^C$, then the individual tooth local tranformations are determined and compared to $T_\tau^C$ to determine $T_\tau$, then after aligning each tooth $\beta_\tau$ may be determined.

At block 380, the distribution estimation for case-specific parameters are determined. For example, each tooth's relative shape, location, and rotation are determined in order to build a distribution for each case-specific parameter. For example the distribution of the $a_\tau^i$, the coefficients for the principal components for the surface model of the each respective tooth in all of the retrieved models, is determined.

The location and orientation of each tooth may be averaged to determine a mean location for each tooth and the orientation of each tooth is averaged to determine a mean orientation for each tooth. The mean location and orientation are used to determine $T_\tau^C$.

At block 390, the mean of the distribution of the estimation for case-specific parameters is used as the generic parameters of mean tooth position and mean tooth shape.

FIG. 5 depicts a method 500 of generating a parametric model of one or more of a patient's teeth and converting the parametric model of one or more teeth into a 3D model of a dental arch, according to some implementations. The method 500 may be used for generating a 3D model of a tooth arch of a patient based on a parametric model of the patient's teeth.

At block 510, a mean shape of each tooth is determined. As an example, the mean shape, $S_\tau^C$ of each tooth is determined. In some embodiments, the mean shape may be based on the mean shape of a set of arches from historical and/or idealized cases, as discussed herein. In some embodiments, the mean shape may be rendered, for example, on a screen for viewing by a patient or dental professional. For example, mean tooth shapes 512 are rendered for viewing. In some embodiments, the mean shape may be loaded into memory or retrieved from memory. The mean shape may also be initialized as a set of matrices, one for each tooth.

At block 520, a principal component analysis shape adjustment is performed on the mean shape of the teeth. This adjustment adjusts the shape of the teeth based on the patient's particular teeth, for example, based on a scan of the patient's teeth, a 2D image, or other imaging technologies, as discussed herein. As an example, a principal component analysis shape adjustment is performed on the mean shape of the teeth, $S_\tau^C$. For each tooth in the model, the case-specific coefficients for the principal components, $a_\tau^i$, are applied to the principal component, $B_\tau^i$. After the shape adjustment is completed, in some embodiments, the adjusted shape may be rendered, for example, on a screen for viewing by a patient or dental professional. For example, adjusted tooth shapes 522 are rendered for viewing. In some embodiments, the adjusted shape may be stored into memory. The adjusted shape may also be stored as a set of matrices, one for each tooth.

At block 530, a mean tooth pose is determined. In some embodiments, the mean tooth pose may be based on the mean tooth pose of a set of arches from historical and/or idealized case, as discussed herein. In some embodiments, at block 530, each adjusted tooth 522 is placed in its corresponding mean location and orientation, as determined by the mean arch. In some embodiments, the mean tooth pose may be rendered, for example, on a screen for viewing by a patient or dental professional. For example, mean tooth pose 532 is rendered for viewing. In some embodiments, the mean tooth pose may be loaded into memory or retrieved from memory. The mean tooth pose may also be initialized as a set of matrices, one for each tooth in the tooth pose. In some embodiments, the mean tooth shapes from block 510 may be placed in their corresponding mean tooth pose at block 530 before the shapes of the teeth are adjusted at block 520. In other words, the order of block 520 and block 530 may be swapped.

At block 540, a tooth pose adjustment is performed on the mean tooth pose. This adjustment adjusts the shape of the teeth based on the patient's particular teeth, for example, based on a scan of the patient's teeth, a 2D image, or other imaging technologies, as discussed herein. In some embodiments, the pose adjustment $T_\tau$ is based on the particular tooth pose of a patient's arches, as discussed above. In some embodiments, at block 540, the position and orientation of each tooth 522 is adjusted such that it is placed in a location and orientation as determined by the location and orientation of the teeth in a patient's imaged arch, or otherwise, as discussed herein. In some embodiments, the adjusted tooth pose may be rendered, for example, on a screen for viewing by a patient or dental professional. For example, adjusted tooth pose 542 is rendered for viewing. In some embodiments, the adjusted tooth pose may be stored in memory. The adjusted tooth pose may also be stored as a set of matrices and/or data structures, e.g., one for each tooth in the tooth pose. In some embodiments, the mean tooth shapes from block 510 may be placed in their corresponding adjusted tooth pose at block 540 before the shapes of the teeth are adjusted at block 520. In other words, the order of block 520 and blocks 530 and 540 may be swapped such that block 520 takes place after blocks 530 and 540.

At block 550, the arch is scaled such that it is generated according to the patient's tooth and arch size. In some embodiments, the arch scaling factor Φ is based on the particular tooth and arch of a particular patient, as discussed above. In various embodiments, the arch scaling factor may also be based on one or more of the image size of the 2D image of the patient, for example, when scaling the 3D model for integration into a 2D image. In some embodiments, at block 550, the size of each tooth 522 and the arch is adjusted such that the scaled arch matches the size of a patient's arch, as determined, for example, by size of the teeth and arch in the patient's imaged arch, or otherwise, as discussed herein. In some embodiments, the scaled arch may be rendered, for example, on a screen for viewing by a patient or dental professional. For example, scaled arch 552 is rendered for viewing. In some embodiments, the scaled arch may be stored in memory. The scaled arch may also be stored as a set of matrices and/or data structures, one for each tooth in the tooth pose. In some embodiments, the mean tooth shapes from block 510 may be placed in their corresponding scaled position and size at block 550 before the shapes of the teeth are adjusted at block 520. In other words, the order of block 520 and blocks 530, 540, and 550 may be swapped such that block 520 takes place after blocks 530, 540, and 550.

The blocks of method 500 may be carried out in orders other than those shown in FIG. 5. For example, blocks 510 and 530 may be performed before blocks 520, 540, and 550. In some embodiments, blocks 510, 520, 530, and 550 may be carried out before block 540. These and other modifications to the order of the blocks in method 500 may be carried out without deviating from the spirit of the disclosure.

Figure 6:
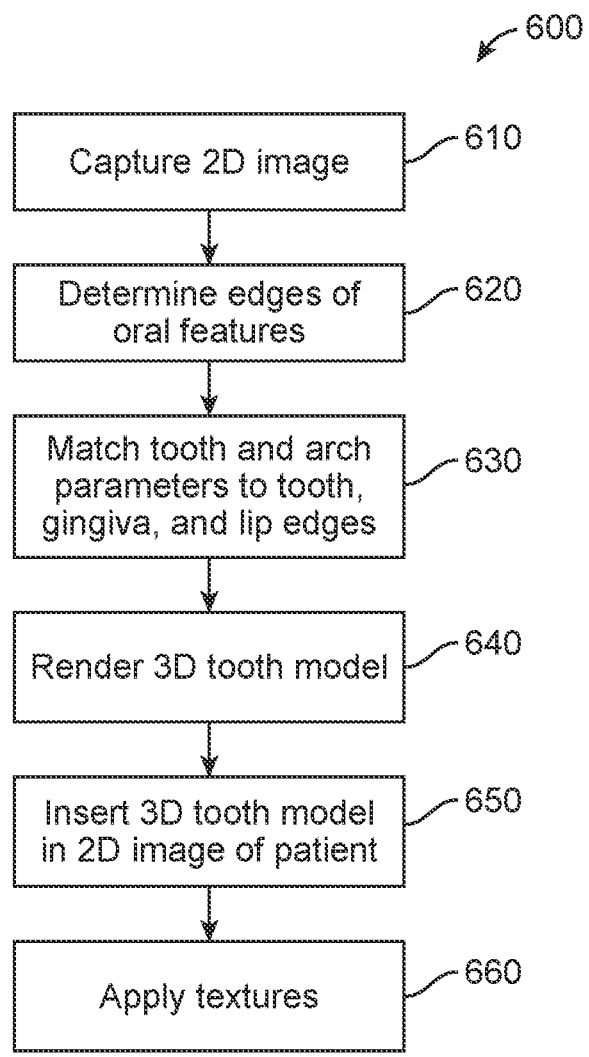
FIG. 6 depicts a method for constructing a 3D model from a 2D image, in accordance with one or more embodiments herein.

With attention to FIG. 6, FIG. 6 illustrates a method 600 for constructing a 3D model from a 2D image, according to one or more embodiments disclosed herein.

At block 610, a 2D image of a patient is captured. In some embodiments, the 2D image includes the mouth of the patient and one or more images of the face, head, neck, shoulders, torso, or the entire patient. The 2D image of the patient may include an image of the patient with their mouth in one or more positions. For example, the patient's mouth may be a smiling position, such as a social smiling position, a repose position with relaxed muscles and lips slightly parted, or anterior retracted open bite or closed bite positions.

In some embodiments, the image of the patient is taken with an image capture system. The image may be captured with a lens at a predetermined focal length and at a distance from the patient. The image may be captured remotely and then received for processing. The image may be gathered from a storage system, a networked location, a social media website, etc. The image may be a series of images of video captured from one or more perspectives. For example, the images may include one or more of a frontal facial image and a profile image, including one or more three-quarter profile images and full profile images.

At block 620, edges of oral features of the patient are determined. For example, the edges of one or more of the patient's teeth, lips, and gingiva may be determined. An initial determination of the patient's lips (for example, the inner edges of the lips that define the mount opening), teeth, and gingiva contours may be identified by a machine learning algorithm, such as a convoluted neural network. The machine learning algorithm may be trained based on pre-identified labels of the lips, teeth, and gingiva visible within a 2D image of a patient. The initial contours may be weighted contours such that the machine learning algorithm's confidence that a given position in the image, such as at each pixel, is an edge or contour of a patient's lips, teeth, or gingiva.

The initial contours may be extracted from the image. The initial contours may have a brightness or other scale applied to them. For example, in a grey scale image of the contours, each pixel may be assigned a value between 0 and 255, which may indicate a confidence that the pixel is a contour or may indicate the magnitude of the contour at that location.

The pixels that denote the contours may then undergo binarization to change the pixels from a scale of, for example, 0 to 255, to a binary scale of, for example, 0 or 1, creating binarized tooth contours. In the binarization process, the value of each pixel is compared to a threshold value. If the value of the pixel is greater than the threshold, then it may be assigned a new first value, such as a value of 1 and if the pixel is less than the threshold, then it may be assigned a new second value, such as a value of 0, for example.

The binarized tooth contours may be thinned, whereby the contour's thickness is reduced to, for example, a single pixel in width, forming a thinned contour. The width of a contour for thinning may be measured as the shortest distance from a contour pixel adjacent to a non-contour pixel on a first side of a contour, to a contour pixel adjacent a non-contour pixel on a second side of the contour. The single pixel representing the thinned contour at a particular location may be located at the midpoint of the width between the pixel at the first side and the pixel at the second side. After thinning the binarized tooth contours, the thinned contour may be a single width contour at a location that corresponds to a midpoint of the binarized contour.

Figure 7A:
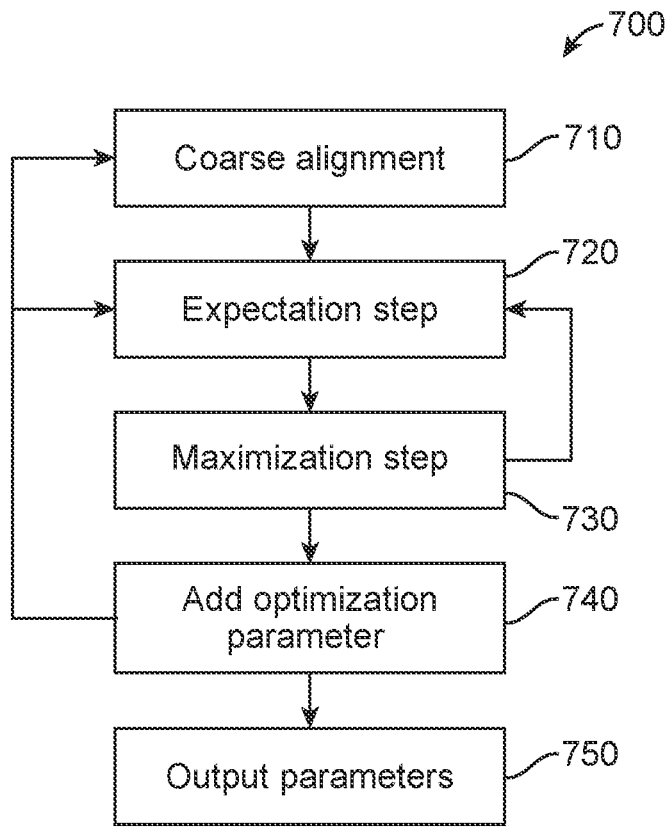
FIG. 7A depicts a method of building a patient-specific parametric model of a patient's teeth, in accordance with one or more embodiments herein.

At block 630, parameterized 3D tooth and arch models are matched to each of the patient's teeth that are depicted in the 2D image of the patient. The matching may be based on the edges, also referred to as contours, determined at block 630. FIG. 7A shows an example of a process of matching tooth and arch models to the edges. Returning to FIG. 6, after identifying and modeling the teeth and arch, or as part of such a process, missing or broken teeth may be inserted into the parameterized 3D tooth and arch model. For example, when a tooth is missing or significantly damaged, the parameterized model of that tooth may be replaced with a mean tooth model, thereby simulating a prosthetic tooth, such as a veneer, crown, or implant prosthetic. In some embodiments, the missing tooth may be left as a space in the arch. In some embodiments a broken tooth may be left, as is, without replacing it with a mean shape tooth.

During the matching process, the case-specific parameters of a parametric arch model are varied and iterated through until a match between the parametric arch model and the teeth depicted in the 2D image is found. This match may be determined based on a projection of the edges of a silhouette of the parametric model match with the edges of the lips, teeth, and gingiva identified in the 2D image.

At block 640, the parametric model of the patient's teeth is rendered. An example of a process of rendering a parametric model of teeth is described with respect to FIG. 8, and elsewhere herein. During the rendering process, a 3D model of the patient's teeth is formed based on data describing the teeth and arch of the patient. For example, based on the parametric 3D model formed at block 630, or otherwise describe herein. In some embodiments, the 3D model is directly inserted into the 2D image of the patient. In such embodiments, the actions in block 640 may be omitted or merged with the actions of block 650 such that, for example, the 3D tooth model is rendered in 2D form for insertion into the 2D image.

Optionally, at block 640, simulated treatments or viewing customizations, such as gingiva line adjustment, jaw position adjustment, missing tooth insertion, or broken tooth repair, can be applied to the 3D model before rendering into 2D form. In some embodiments, the edges of the parametric model (for example, lips, gingiva line, missing or broken teeth) may be altered to display simulated results of cosmetic or other treatments and procedures or to adjust the 2D patient image for customized viewing. For example, a user, such as a dental professional or patient, may adjust the gingiva line to simulate gum treatments. As another example, the user may opt to show, hide, or repair missing or chipped teeth to simulate tooth repair or replacement procedures. In another example, the user may opt to adjust jaw position in the pre- or post-treatment simulated image to simulate appearances with the jaw open, closed, or partially open. A jaw position parameter can be defined by a distance between a tooth surface in the upper jaw and a tooth surface in the lower jaw, such as the distance between the incisal surface of the upper central incisor in relation to the incisal surface of the lower central incisor. The jaw position parameter can be defined and varied by the user. For example, the distance between the incisal surface of the upper central incisor and the incisal surface of the lower central incisor may be varied between −5 mm (indicating, the lower incisors overlapping with the upper incisors by 5 mm) and 10 mm (indicating, a gap of 10 mm between the upper incisors and the lower incisors). The gingiva line can be adjusted by replacing the patient gingiva line mask shape with the mean gingiva line mask shape from the historic shape datastore. Display of gingiva line adjustment can be optionally selected or adjusted by the user. Missing or broken teeth can be replaced with a mean tooth shape from the historic shape datastore. Display of missing tooth replacement or broken tooth repair can be optionally selected by the user. Simulated treatments or viewing customizations may be rendered, for example, on a screen for viewing by a user, patient, or dental professional.

At block 650, the 3D tooth model is inserted into the 2D image of the patient. The inner lip edges determined at block 620 may be used to define the outline of the patient's mouth in the 2D image. At block 650, the area of the 2D image defined by the mouth opening may be removed and the 3D model may be placed behind the 2D image and within the mouth opening. In some embodiments, inserting the 3D tooth model into the 2D image further comprises rendering an image of a parameterized gingiva line in the 2D image. The parameterized gingiva line may be determined, for example, as shown and described, with respect to method 2001 of FIG. 20.

At block 660, textures are applied to the teeth. An example of applying textures is discussed in more detail with respect to FIG. 9. In some implementations, when applying textures to the teeth, the 2D image of the patient is projected onto a 3D model of the teeth, such as the parametric 3D model of the patient's teeth determined, for example, at block 630. When projecting the 2D image into the 3D model, the pixels at each location in the 2D image are assigned to a location on the 3D model. In some embodiments, the pixel value or texture information from 2D image is processed before being applied to 3D model. Other techniques, such as inpainting, blurring, image processing filters, pix2pix transformation technologies, etc., can also be used to generate textures for application to the surfaces of the 3D model. The projected pixels at each location on a surface of the 3D model form a texture for that model. For example, the pixels projected onto a particular tooth of the patient form a texture for that tooth model. This texture can be applied to the 3D tooth model.

FIG. 7A depicts a method 700 of building a patient-specific parametric model of a patient's teeth according to some embodiments.

At block 710, a course alignment of each corresponding mean parametric tooth is aligned with a respective center of a tooth in the 2D image. A center of the parametric tooth may be determined based on the area center of a projection of the parametric tooth's silhouette. A center of a tooth identified in the 2D image of the patient may be determined based on an area center of an area defined by tooth edges and a corresponding lip and/or gingiva edge. The respective centers of the 2D image tooth and the parametric tooth may be aligned before the expectation step and maximization steps of blocks 720 and 730, respectively.

The method 700 may dynamically generate the parametric tooth models with lip and gingiva edges for matching with the teeth in the 2D image and block 710. In addition or alternatively, the lip and gingiva edges maybe applied and/or dynamically adjusted at any of blocks 720, 730, and 740. The 3D tooth models may be computed on the fly for varying lip and gingiva line placement. Using such models provides for a much more accurate parametric model than using gingiva lines alone.

Figure 7B:
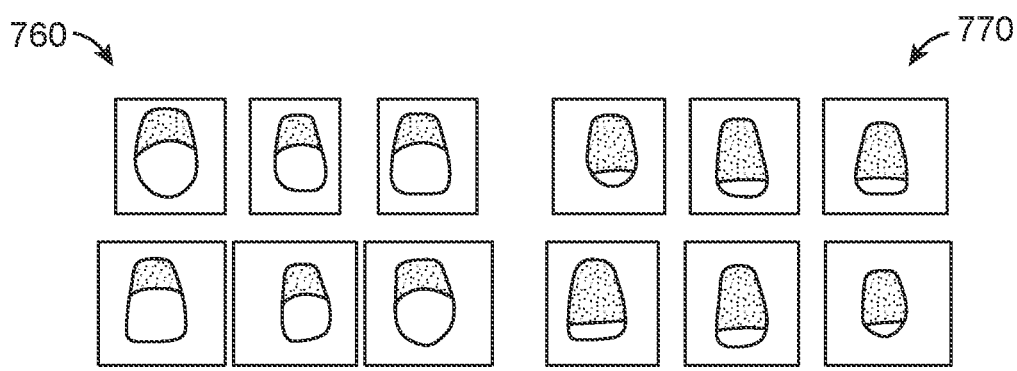
FIG. 7B depicts tooth models with gingiva and lip edges, in accordance with one or more embodiments herein.

When lip and gingiva information is applied at block 710, in some embodiments, only the portion of the parametric model beyond the lip and/or gingiva edges is used to determine the area center of the tooth. Turning to FIG. 7B, the figure depicts examples of tooth models with gingiva edges 760 and tooth models with lip edges 770. At any of blocks 710, 720, 730, 740, the location of the gingiva and/or lip edges may be modified to adjust the fit of the silhouette of the tooth with the visible portion of a corresponding tooth in the 2D image.

The addition of the lip or gingiva edges of the teeth significantly improve the efficiency and operation of process. The result is that the process much more realistically matches teeth models to the 2D image and the process works with a much wider variety of photos, as compared to a process that does not apply lip and gingiva edges to teeth models.

Returning to FIG. 7A, at block 720, an expectation step is performed. In some implementations, an Expectation Management (EM) engine and/or an engine configured to create a 3D model performs block 720. At the expectation step, a silhouette of the tooth is projected onto the 2D image and the edges of the silhouette are evaluated against the edges of the tooth in the 2D image as determined based on the lip, gingiva, and tooth edges. The evaluation may be a determination of the normal at a location at the edge of the silhouette and the closest location in the 2D image with a similar normal. Then the probability that the two edges are the same is determined. This process may be repeated for each location at the edge of the silhouette.

At block 730, a maximization step of the EM engine is performed. At the maximization step a small angle approximation is used in order to provide for an analytical solution to the maximization. The small angle approximation and analytical solution provides a much improved solution as compared to other methods, such as the Gaussian-Newton iterative method. The small angle approximation significantly reduces computation time and resolves to an accurate solution much faster.

Blocks 720 and 730 may be performed iteratively on a single parameter or subset of parameters, performing the expectation step then the maximization step, then back to the expectation step and so on until a threshold of convergence for the single parameter or subset of parameters is reached. Then the process may proceed to block 740.

At block 740, an optimization parameter or subset of parameters are added to the parametric model. For example, optimization of the parametric model may begin with Φ and T, then after iterating through the EM blocks 720 and 730, additional parameters are added. For example, $T_\tau$ may be added and then optimized through the EM blocks 720 and 730 for additional iterations. The number of iterations before adding additional parameters may vary. In some embodiments, the EM blocks 720 and 730 may be iterated through 3, 5, 7, 10, 15, 20, or an arbitrary number (e.g., any integer) of times. Finally, $a_\tau^i$ may be added to the parametric model, which is processed though the EM blocks 720 and 730 until convergence is reached. During this process, outliers may be determined and filtered out. In some embodiments, after block 740, rather than looping back to block 720 and proceeding directly to the expectation step, the process 700 may loop back to block 710, where a coarse alignment procession is performed based on the updated parametric model.

At block 750 the parameters of a parametric model are output to another engine or even to a datastore for later retrieval. For example, a rendering engine may retrieve the parameters for the parametric model for rendering, as described with respect to FIG. 8, and elsewhere herein.

Figure 8:
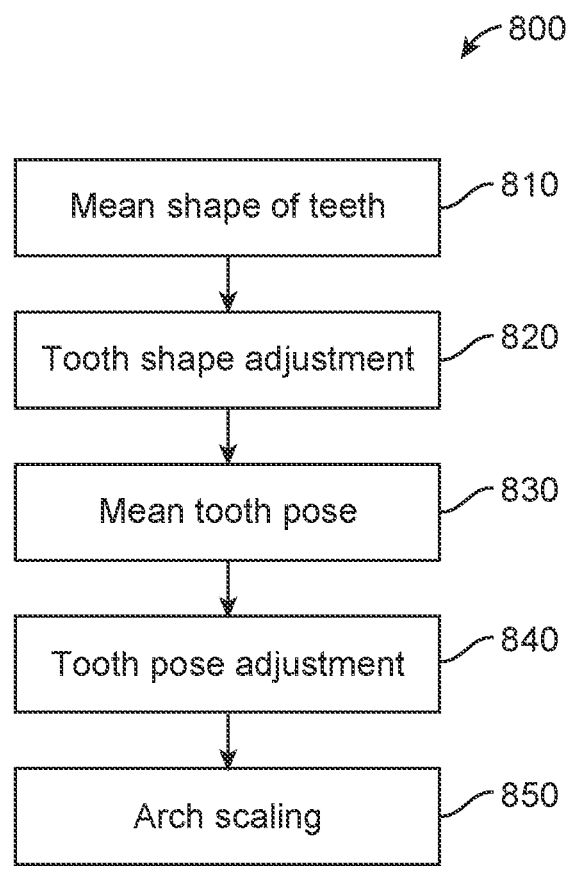
FIG. 8 depicts a method of rendering patient's teeth in an initial position using a parametric model of the patient's arch, in accordance with one or more embodiments herein.

FIG. 8 depicts a method 800 of rendering patient's teeth in an initial position, using a parametric model of the patient's arch, in accordance with one or more embodiments herein.

At block 810, the mean shape, $S_\tau^C$, of each tooth is determined. In some embodiments, the mean shape may be based on the mean shape of a set of arches taken, e.g., from historical cases and/or those representing idealized arch forms, as discussed herein. In some embodiments, the mean shape may be rendered, for example, on a screen for viewing by a patient or dental professional. In some embodiments, the mean shape may be loaded into memory or retrieved from memory. The mean shape may also be initialized as a set of matrices, one for each tooth.

At block 820, a principal component analysis shape adjustment is performed on the mean shape of the teeth, $S_\tau^C$. For each tooth in the model, the case specific coefficients for the principal components, $a_\tau^i$, are applied to the principal component, $B_\tau^i$. After the shape adjustment is completed, in some embodiments, the adjusted shape may be rendered, for example, on a screen for viewing by a patient or dental professional. For example, adjusted tooth shapes are rendered for viewing. In some embodiments, the adjusted shape may be stored into memory. The adjusted shape may also be stored as a set of matrices, one for each tooth.

At block 830, the mean tooth pose is determined. In some embodiments, the mean tooth pose may be based on the mean tooth pose of a set of scanned arches, as discussed herein. In some embodiments, at block 830, each adjusted tooth is placed in its corresponding mean location and orientation, as determined by the mean arch. In some embodiments, the mean tooth pose may be rendered, for example, on a screen for viewing by a patient or dental professional. In some embodiments, the mean tooth pose may be loaded into memory or retrieved from memory. The mean tooth pose may also be initialized as a set of matrices and/or other data structures, e.g., one for each tooth in the tooth pose. In some embodiments, the mean tooth shapes from block 810 may be placed in their corresponding mean tooth pose at block 830 before the shapes of the teeth are adjusted at block 820. In other words, the order of block 820 and block 830 may be swapped.

At block 840, a tooth pose adjustment is performed on the mean tooth pose. In some embodiments, the pose adjustment $T_\tau$ is based on the particular tooth pose of a patient's arches, as discussed above. In some embodiments, at block 840, the position and orientation of each tooth is adjusted such that it is placed in a location and orientation as determined by the location and orientation of the teeth in patient's arch, or otherwise, as discussed herein. In some embodiments, the adjusted tooth pose may be rendered, for example, on a screen for viewing by a patient or dental professional. In some embodiments, the adjusted tooth pose may be stored in memory. The adjusted tooth pose may also be stored as a set of matrices and/or other data structures, e.g., one for each tooth in the tooth pose. In some embodiments, the mean tooth shapes from block 810 may be placed in their corresponding adjusted tooth pose at block 840 before the shapes of the teeth are adjusted at block 820. In other words, the order of block 820 and blocks 830 and 840 may be swapped such that block 820 takes place after blocks 830 and 840.

At block 850, the arch is scaled such that it is generated with tooth dimensions according to the patient's tooth and arch size. In some embodiments, an arch scaling factor t is based on the particular tooth and arch of a particular patient, as discussed above. In some embodiments, at block 850, the size of the arch is adjusted such that the scaled arch matches the size of a patient's arch, as determined, for example, by size of the teeth and arch in the patient's arch, or otherwise, as discussed herein. In some embodiments, the scaled arch may be rendered, for example, on a screen for viewing by a patient or dental professional. In some embodiments, the scaled arch may be stored in memory. The scaled arch may also be stored as a set of matrices and/or data structures, e.g., one for each tooth in the tooth pose. In some embodiments, the mean tooth shapes from block 810 may be placed in their corresponding scaled position and size at block 850 before the shapes of the teeth are adjusted at block 820. In other words, the order of block 820 and blocks 830, 840, and 850 may be swapped such that block 820 takes place after blocks 830, 840, and 850.

The blocks of the method 800 may be carried out in orders other than those shown in FIG. 8. For example, blocks 810 and 830 may be performed before blocks 820, 840, and 850. In some embodiments, blocks 810, 820, 830, and 850 may be carried out before block 840. These and other modifications to the order of the blocks in method 800 may be carried out without deviating from the spirit of the disclosure.

Figure 9:
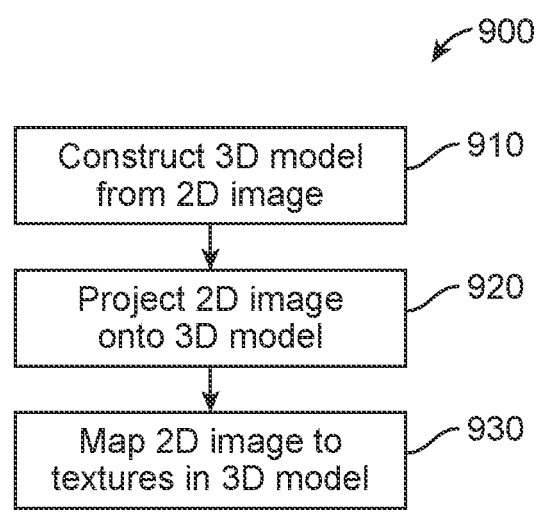
FIG. 9 depicts a method of constructing and applying textures to a 3D model, in accordance with one or more embodiments herein.

FIG. 9 depicts a method 900 of constructing and applying textures to a 3D model, in accordance with one or more embodiments herein. Textures may aid in providing detail, such as color information, to the 3D model of a patient's teeth. As described herein, the process 900 uses images of the patient's teeth to provide lifelike textures for a patient's teeth.

Accordingly, at block 910, a 3D model of the patient's teeth and a 2D image of the patient are acquired, as described elsewhere herein, for example, in the discussion related to FIG. 5. The 2D image and the 3D model should depict the teeth in the same positions, for example, the 3D model could be a parametric model derived from the 2D image of the patient.

At block 920, the 2D image of the patient's teeth is projected onto the 3D model and the image is aligned with the model. Such alignment may be carried out by matching contours in the 3D model with contours in the 2D image. Contours may include lip, gingiva, and teeth edges, determined as described elsewhere herein.

At block 930, the color information from the 2D image is mapped as textures to the 3D model. Color information may include lighting conditions, such as specular highlights, accurate tooth coloration and textures, and other tooth features, such as tooth jewelry, gold teeth, etc. Once the textures are mapped to the 3D model, the teeth in the 3D model may be repositioned, for example to depict an estimated and/or intended outcome of a dental treatment plan (e.g., an orthodontic treatment plan, a restorative treatment plan, some combination, thereof, etc.). Such a final position includes both accurate color and tooth feature information and accurate 3D positioning of the patient's teeth and may be used for example, in simulating an estimated and/or intended outcome of a dental treatment plan (e.g., a final orthodontic position) of a patient's teeth, as described with respect to FIG. 10A, FIG. 10B, and/or elsewhere herein.

In some embodiments, the textures model is adjusted to simulate clinical or beautification treatments. For example, color may be adjusted to simulate tooth whitening procedures. Simulating such treatments may include generating a mask from a 2D projection of the 3D tooth model with the model in an arrangement for insertion in the 2D image, for example, in either the initial or final positions. The mask can be applied to the 2D image of the patient's teeth in either the initial or final positions. Color adjustment or whitening can be further applied to the mask region. Color adjustment and whitening parameters can be optionally selected and adjusted by the user. Color adjustments and whitening may be rendered, for example, on a screen for viewing by a user, patient, or dental professional.

Figure 10A:
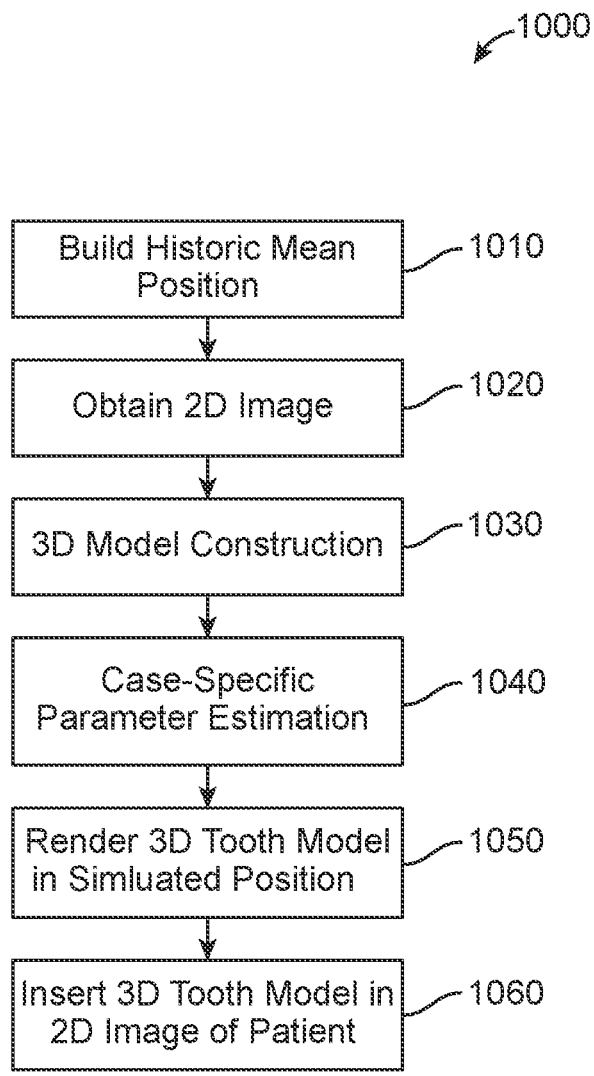
FIG. 10A depicts a method of simulating an estimated outcome of an orthodontic treatment on a patient's teeth, in accordance with one or more embodiments herein.

FIG. 10A depicts a method 1000 for simulating an estimated and/or intended outcome of a dental treatment plan on a patient's teeth, in accordance with one or more embodiments herein.

At block 1010, a model of a mean set of teeth arches is built. In some embodiments, the model is a parametric 3D model of a mean arch based on a set of historic scanned arches and/or arches representing idealized arch forms. In some embodiments, the scans are from the initial positions of patient's teeth. In some embodiments the scans are from patients after they have completed orthodontic treatment. In still other embodiments, the scans are taken without regard to whether the patient has undergone orthodontic treatment or not. In some implementations, the historic and/or idealized cases may represent arch models of treated patients (e.g., of patients who in the past have undergone treatment) and/or idealized arch models representing intended outcomes of various forms of orthodontic treatment. Block 1010 may include the process 350 as described with respect to FIG. 3B. At block 1010, cases are acquired. The cases may be retrieved from a datastore and may include previously scanned and segmented arch models.

The arches may also be aligned. Each arch in the datastore may aligned at a plurality of locations. For instance, each arch may be aligned at the following three locations: between the central incisors and at each distal end of the left and right side of each arch. For example, FIG. 4 shows a set of arches 400 aligned at location between the central incisors 410, at the left distal end of the arch 430, and the right distal end of the arch 420.

In some embodiments, determining a mean arch model and determining arch model distributions includes performing sub steps. For example, each historic arch may be rescaled to determine $\Phi$, then each arch is averaged to determine $T_\tau^C$, then the individual tooth local transformations are determined and compared to $T_\tau^C$ to determine $T_\tau$, then after aligning each tooth f is determined.

The distribution estimation for case-specific parameters are also determined. For example, each tooth's relative shape, location, and rotation are determined in order to build the distribution for each case-specific parameter. For example the distribution of the $a_\tau^i$, the coefficients for the principal components, for the surface model of the each respective tooth in all of the retrieved models is determined.

The location and orientation of each tooth is averaged to determine a mean location for each tooth and the orientation of each tooth is averaged to determine a mean orientation for each tooth. The mean location and orientation are used to determine $T_\tau^C$.

Finally, the mean of the distribution of the estimation for case-specific parameters may be used as the generic parameters of mean tooth position and mean tooth shape.

At block 1020, a 2D image of a patient is captured. In some embodiments, the 2D image includes the mouth of the patient and one or more images of the face, head, neck, shoulders, torso, or the entire patient. The 2D image of the patient may include an image of the patient with their mouth in one or more positions; for example, the patient's mouth may be a smiling position, such as a social smiling position, a repose position with relaxed muscles and lips slightly parted, or anterior retracted open bite or closed bite positions.

In some embodiments, the image of the patient is obtained, e.g., taken with an image capture system. The image may be captured with a lens at a predetermined focal length and at a distance from the patient. In some implementations, the image of the patient is obtained from a computer-storage device, a network location, a social media account, etc. The image may be captured remotely and then received for processing. The image may be a series of images or video captured from one or more perspectives. For example, the images may include one or more of a frontal facial image and a profile image, including one or more three-quarter profile images and full profile images.

At block 1030, a 3D model of the patient's teeth is constructed from the 2D image of the patient's teeth. The 3D model may be based on a parametric model constructed according to the process described with respect to FIG. 6, wherein the edges of the oral features of the patient are determined. For example, the edges of one or more of the patient's teeth, lips, and gingiva may be determined. An initial determination of the patient's lips (for example, the inner edges of the lips that define the mount opening), teeth, and gingiva contours may be identified by a machine learning algorithm, such as a convoluted neural network.

Then, the initial contours may be extracted from the image. The pixels that denote the contours may then undergo binarization. The binarized tooth contours are thinned, whereby the contour's thickness is reduced to, for example, a single pixel in width, forming a thinned contour.

Using the contours, either thinned or otherwise, parameterized 3D teeth and arch models are matched to each of the patient's teeth that are depicted in the 2D image of the patient. The matching is based on the contours, determined above. After identifying and modeling the teeth and arch, or as part of such a process, missing or broken teeth may be inserted into the parameterized 3D tooth and arch model.

At block 1040, case-specific parameters are estimated. In some embodiments, the case-specific parameters may be determined at block 1030 as part of the model construction according to the process described, for example, at FIG. 6. During the matching process or at block 1040, the case-specific parameters of a parametric arch model are varied and iterated through until a match between the parametric arch model and the teeth depicted in the 2D image is found. This match may be determined based on a projection of the edges of a silhouette of the parametric model match with the edges of the lips, teeth, and gingiva identified in the 2D image, as described herein.

Figure 11:
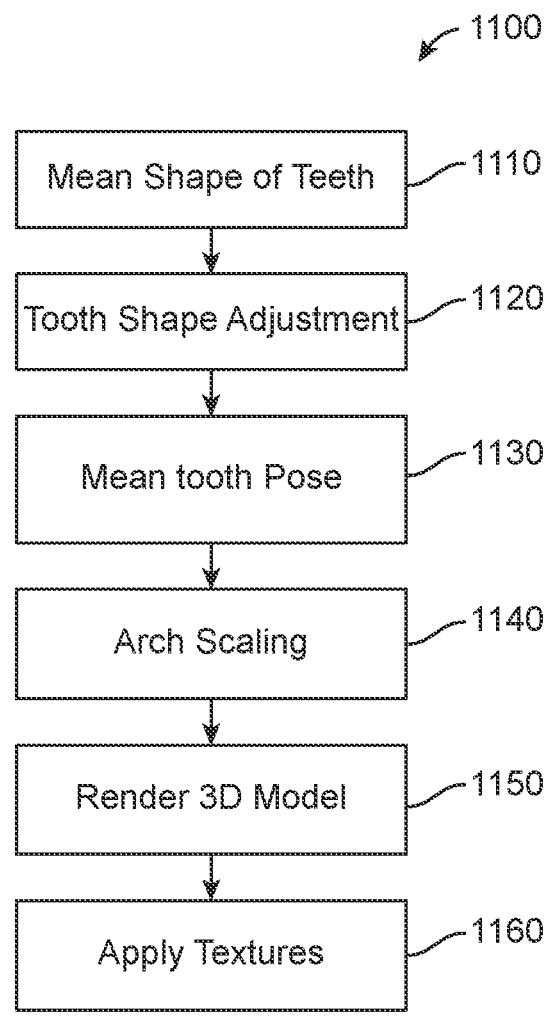
FIG. 11 shows an example of a method for rendering teeth according to an estimated outcome of a dental treatment plan, in accordance with one or more embodiments herein.

At block 1050, the patient's teeth are rendered according to a simulated outcome of a dental treatment plan using the patient's case-specific parameters for tooth shape or arch scale, but using the mean value for tooth position. FIG. 11 shows an example of a method for rendering teeth according to an and/or intended outcome of a dental treatment plan using the appropriate case-specific and mean parameter values.

Optionally, at block 1050, other changes, such as gingiva line adjustment, jaw position adjustment, missing tooth replacement, or broken tooth repair, can be applied to the 3D model before rendering into 2D form. In some embodiments, the edges and other features of the model, such as lips, gingiva line, and missing or broken teeth, may be altered to display simulated results of treatment procedures or to adjust the 2D patient image for customized viewing. For example, the user may adjust the gingiva line to simulate gum treatments. In another example, the user may opt to show, hide, or repair missing or chipped teeth to simulate tooth repair or replacement procedures. In this case an ideal tooth, based on the ideal parameters discussed above, may be used to replace the missing or damaged tooth. The missing or damaged tooth may be replaced based on one of the teeth in the historic datastore, or with a patient's own tooth, such as a corresponding tooth from the opposite side of the patient's arch may be used. For example, if the left upper canine is missing or chipped, a mirrored model of the patient's right upper canine may be used in the position of the missing left upper canine. In another example, the user may opt to adjust jaw position in the pre- or post-treatment simulated image to simulate appearances with the jaw open, closed, or partially open. A jaw position parameter can be defined by distance between a tooth surface in the upper jaw and a tooth surface in the lower jaw, such as the distance between the incisal surface of the upper central incisor in relation to the incisal surface of the lower central incisor. The jaw position parameter can be defined and varied by the user. The gingiva line can be adjusted by replacing the patient gingiva line mask shape with the mean gingiva line mask shape from the historic mean shape database. Display of gingiva line adjustment can be optionally selected or adjusted by the user. Missing or broken teeth can be replaced with a mean tooth shape from the historic mean shape database. Display of missing tooth replacement or broken tooth repair can be optionally selected by the user. Simulated treatments or viewing customizations may be rendered, for example, on a screen for viewing by the user, a patient, or a dental professional.

At block 1060, the 3D model is inserted into 2D image of the patient. For example, the 3D rendering of the teeth may be placed in the mouth of the patient as defined by the lip contours determined at block 1030 as part of the model construction process. In some embodiments, inserting the 3D tooth model into the 2D image further comprises rendering an image of a parameterized gingiva line in the 2D image. The parameterized gingiva line may be determined, for example, as shown and described, with respect to method 2001 of FIG. 20. In some embodiments, at block 1060 the textures model is adjusted to simulate clinical beautification treatments. For example, color may be adjusted to simulate tooth whitening procedures. A mask can be generated from at 2D projection of the 3D tooth model. The mask can be applied to the 2D image of the patient's teeth, in either the initial or final positions. Color adjustment or whitening can be further applied to the mask region. Color adjustment and whitening parameters can be optionally selected and adjusted by the user.

Simulated treatments or viewing customizations performed at block 1050 or block 1060 can be selected, de-selected, or adjusted by the user on the projected 2D image. Parameters can be adjusted to simulate treatments, such as whitening, gum line treatments, tooth replacement, or tooth repair, or for viewing customization, such as to display jaw open, closed, or partially open. In one example, the user can optionally adjust a color parameter to simulate tooth whitening. The user can adjust the color parameter to increase or decrease the degree of tooth whitening. In another example, the user can optionally adjust a gingiva line parameter to simulate gum line treatments or changes as a result of dental hygiene. The user can adjust the gingiva line parameter to raise the gingiva line (decrease the amount of exposed tooth surface) to simulate gum recovery, such as resulting from improved dental hygiene or gum line treatments, or lower the gingiva line (increase the amount of exposed tooth surface) to simulate gum recession, such as resulting from poor dental hygiene. In another example, the user can optionally select a tooth replacement parameter.

The user can select the tooth replacement parameter to replace one or more missing, broken, or damaged teeth with an ideal tooth, such as with a tooth from the historic datastore or with a patient's own tooth. In another example, the user can optionally adjust a jaw line parameter for customized viewing of jaw position. The user can increase a distance between a tooth in the upper jaw in relation to a tooth in the lower jaw to simulate jaw opening or decrease the distance between the tooth in the upper jaw in relation to the tooth in the lower jaw to simulate jaw closing. In this case, the user can simulate the appearance of orthodontic, cosmetic, or clinical treatments in a variety of jaw positions.

Figure 10B:
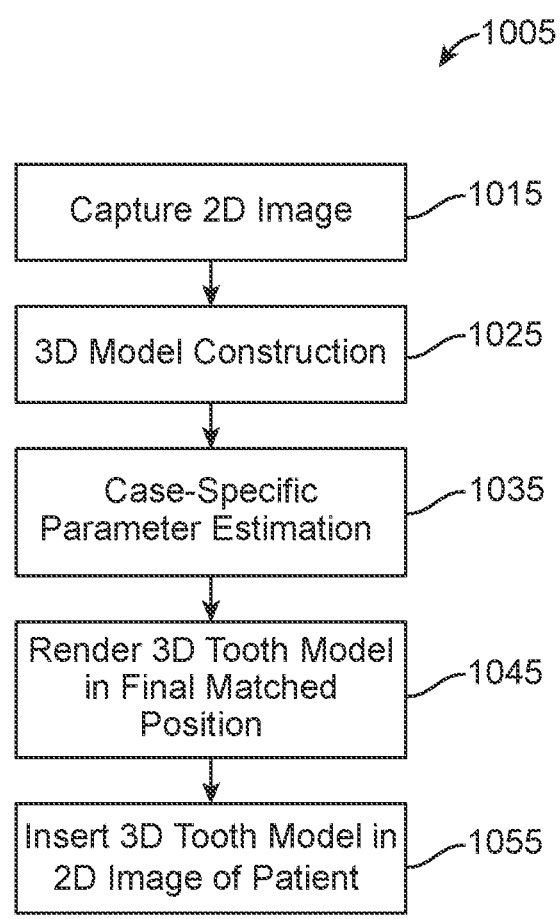
FIG. 10B depicts a method of simulating orthodontic treatment of a patient, based on matching tooth shape parameters, in accordance with one or more embodiments herein.

FIG. 10B depicts a process 1005 for simulating a final treatment position of a patient's teeth using a matched arch identified from a parameterized search of the treatment plan datastore.

At block 1015, a 2D image of a patient is captured, as described at block 1020 of FIG. 10A, and, at block 1025, the 3D model of the patient's teeth is constructed from the 2D image of the patient's teeth as at block 1030 of FIG. 10A. At block 1035 case-specific parameters are estimated as at block 1040 of FIG. 10A.

At block 1045 the tooth shape parameters of the patient's teeth from the 3D model are used to perform a parameterized search of the treatment plan datastore. When matching the shapes of teeth of the patient with the shapes of teeth of historic treatment in the datastore, the shapes of the teeth in the patient's parameterized 3D model are compared to the parameterized shapes of the teeth in each of the historic records in the treatment datastore. When a match between the teeth shapes is found, the final tooth positions and orientations, or the final arch model of the match record may be used in the simulated treatment plan. A parameterized template arch may be identified based on comparison of tooth shape parameters to identify a matched template arch. In some embodiments, the match may be based on, for example, the closest match template arch. In some embodiments, the template shape may be loaded into memory or retrieved from memory. The template shape may also be initialized as a set of matrices, one for each tooth. Once a match is found in a record within treatment datastore, the final arch model from the match record is retrieved and may be used as a basis for the patient's target final tooth positions.

In some embodiments, the tooth locations and orientations in the matched record are used as the basis for the tooth locations and orientations for the patient's target final tooth positions. When using the tooth locations and orientations, the patient's parameterized arch model may be modified with the tooth locations and orientations in the matched record or the match record may be updated with the shape of the patient's teeth. In some embodiments, the model of each of the patient's teeth with an unaltered tooth shape is placed in the final tooth pose determined from the matched record. In some embodiments, the model of each of the patient's teeth with an adjusted shape, such as the teeth shapes from the matched record, is placed in the final tooth pose determined from the matched record. Optionally, a tooth pose adjustment can be performed to adjust the positions of the teeth in the final tooth pose.

In some embodiments, the final arch model from the matched record is used as the simulated final position for the patient's treatment in the 2D rendering. In some embodiments, the teeth of the final arch model from the matched record are placed in positions according to the positions of the teeth in the patient's 2D photo. Alternately, the teeth of the final arch model are placed in positions according to the positions of the teeth in the patient's parameterized 3D model. The final arch model, optionally with positions adjusted according to the patient's 2D photo or 3D model, may be used as the simulated position in the 2D rendering.

The shape of the template teeth may be adjusted based on the patient's parameterized 3D model to more closely match the patient's tooth shapes. Optionally, a principal component analysis shape adjustment can be performed on the template teeth shape. After the shape adjustment is completed, in some embodiments, the adjusted shape may be rendered, for example, on a screen for viewing by a user, patient, or dental professional. In some embodiments, the adjusted shape may be stored into memory. The adjusted shape may also be stored as a set of matrices, one for each tooth. In some embodiments, the patient's teeth are substituted for the teeth in the matching template from the treatment datastore.

The template arch may be scaled such that it is generated with according to the patient's tooth and arch size. In some embodiments, the template arch scaling factor $\Phi$ is based on the particular tooth and arch of a particular patient, as discussed above. In some embodiments, the template arch scaling factor may also be based on one or more of the image size of the 2D image of the patient, for example, when scaling the 3D model for integration into a 2D image. In some embodiments, the size of each template tooth and the template arch is adjusted such that the scaled template arch matches the size of a patient's arch as determined, for example, by the size of the teeth and arch in the patient's scanned arch, or otherwise, as discussed herein. In some embodiments, the scaled template arch may be rendered, for example, on a screen for viewing by a user, patient, or dental professional. In some embodiments, the scaled template arch may be stored in memory. The scaled template arch may also be stored as a set of matrices, one for each tooth in the tooth pose. In some embodiments, the ideal template tooth shapes may be placed in their corresponding scaled position and size before the shapes of the teeth are adjusted.

At block 1045, simulated treatments or viewing customizations, such as gingiva line adjustment, jaw position, missing tooth insertion, or broken tooth repair, can be applied to the 3D model before rendering into 2D form. Simulated treatments or viewing customizations changes may be applied and adjusted as described at block 640.

At block 1055 the 3D model is inserted into a 2D image of the patient. For example, the 3D rendering of the teeth may be placed in the mouth of the patient as defined by the lip contours determined at block 1025 as part of the model construction process. Rendering may be performed with or without the simulated treatments or viewing customizations implemented at block 1045. In some embodiments, inserting the 3D tooth model into the 2D image further comprises rendering an image of a parameterized gingiva line in the 2D image. The parameterized gingiva line may be determined, for example, as shown and described with respect to method 2001 of FIG. 20. In some embodiments, at block 1055 the textures model is adjusted to simulate clinical treatments. For example, color may be adjusted to simulate tooth whitening procedures. A mask can be generated from a 2D projection of the 3D tooth model. The mask can be applied to the 2D image of the patient's teeth, in either the initial or final positions. Color adjustment or whitening can be further applied to the mask region. Color adjustment and whitening parameters can be optionally selected and adjusted by the user.

Simulated treatments and viewing customizations performed at block 1045 or block 1055 can be selected, de-selected, or adjusted by the user on the projected 2D image. Parameters can be adjusted to simulate treatment, such as whitening, gum line treatments, tooth replacement, or tooth repair, or for viewing customization, such as display jaw open, closed, or partially open.

FIG. 11 shows an example of a method 1100 for rendering teeth according to an estimated and/or intended outcome of a dental treatment plan based on a parametric model of the patient's arch using patient-derived values for the case-specific parameters of scale and tooth shape, but using a mean value (e.g., one derived from historical and/or idealized arches) for tooth position.

At block 1110 the mean shape, $S_\tau^C$, of each tooth is determined. In some embodiments, the mean shape may be based on the mean shape of a set of scanned arches, as discussed herein. In some embodiments, the mean shape may be rendered, for example, on a screen for viewing by a patient or dental professional. In some embodiments, the mean shape may be loaded into memory or retrieved from memory. The mean shape may also be initialized as a set of matrices, one for each tooth.

At block 1120, a principal component analysis shape adjustment is performed on the mean shape of the teeth, $S_\tau^C$. For each tooth in the model, the case specific coefficients for the principal components, $a_\tau^i$, are applied to the principal component, $B_\tau^i$. After the shape adjustment is completed, in some embodiments, the adjusted shape may be rendered, for example, on a screen for viewing by a patient or dental professional. In some embodiments, the adjusted shape may be stored into memory. The adjusted shape may also be stored as a set of matrices and/or data structures, e.g., one for each tooth.

At block 1130, the mean tooth pose is determined. In some embodiments, the mean tooth pose may be based on the mean tooth pose of a set of scanned arches, as discussed above. In some embodiments, at block 1130, each adjusted tooth is placed in its corresponding mean location and orientation, as determined by the mean arch. In some embodiments, the mean tooth pose may be rendered, for example, on a screen for viewing by a patient or dental professional. In some embodiments, the mean tooth pose may be loaded into memory or retrieved from memory. The mean tooth pose may also be initialized as a set of matrices, one for each tooth in the tooth pose. In some embodiments, the mean tooth shapes from block 1110 may be placed in their corresponding mean tooth pose at block 1130 before the shapes of the teeth are adjusted at block 1120. In other words, the order of block 1120 and block 1130 may be swapped.

At block 1140, the arch is scaled such that it is generated with tooth dimensions according to the patient's tooth and arch size. In some embodiments, an arch scaling factor Φ is based on the particular tooth and arch of a particular patient, as discussed above. In some embodiments, at block 1140 the arch is adjusted such that the scaled arch matches the size of a patient's arch, as determined, for example, by size of the teeth and arch in the patient's scanned arch, or otherwise, as discussed herein. In some embodiments, the scaled arch may be rendered, for example, on a screen for viewing by a patient or dental professional. In some embodiments, the scaled arch may be stored in memory. The scaled arch may also be stored as a set of matrices, one for each tooth in the tooth pose. In some embodiments, the mean tooth shapes from block 1110 may be placed in their corresponding scaled position and size at block 1140 before the shapes of the teeth are adjusted at block 1120. In other words, the order of block 1120 and blocks 1130, and 1140 may be swapped such that block 1120 takes place after blocks 1130 and 1140.

Prior to rendering at block 1150 simulated treatment or viewing customizations, such as gingiva line adjustment, jaw position, missing tooth insertion, or broken tooth repair, can be applied to the 3D model. Simulated treatment or viewing customizations may be applied and adjusted as described at block 640. Simulated treatment or viewing customizations can be applied before or after arch scaling (e.g., before or after block 1140).

At block 1150, the 3D model of the patient's teeth determined at block 1140 is rendered for viewing or the final 3D model is stored for later on-screen rendering. The 3D model can be rendered for viewing or stored for later on-screen rendering with or without the simulated treatment or viewing customizations.

At block 1160, textures are applied to the 3D model of the patient's teeth in an estimated and/or intended final position. For example, textures determined based on a 2D image of the patient's teeth, for example, according to process 900 in FIG. 9, may be applied to the 3D model. In some embodiments, the texture application process of block 1160 may occur during or as part of the rendering process of block 1150. Textures can be applied to a mask region, where the mask region may define a region corresponding to an oral feature, for example, lips, gingiva, or teeth. The mask region or a portion thereof may be determined, for example, by simulating the gingiva as shown and described with respect to method 2001 in FIG. 20. During texture application, either at block 1160 or during the rendering process of block 1150, textures model can be adjusted to simulate treatment or for customizable viewing. Simulated treatment or viewing customizations, including color adjustments, e.g., to simulate tooth whitening, can be applied either to the 3D model or may occur as part of the rendering process. Alternatively, color adjustment can be performed at described at block 1060. Simulated treatment and viewing customizations, color adjustment can be adjusted by the user.

Optionally, step 1110 can be replaced by a parameterized search of the treatment plan datastore to identify a matched template model based on the patient's tooth shape. Steps 1120 through 1160 can subsequently be implemented as described using the template arch and tooth shape in place of the mean arch or tooth shape to determine ideal tooth pose instead of mean tooth pose.

Figure 20:
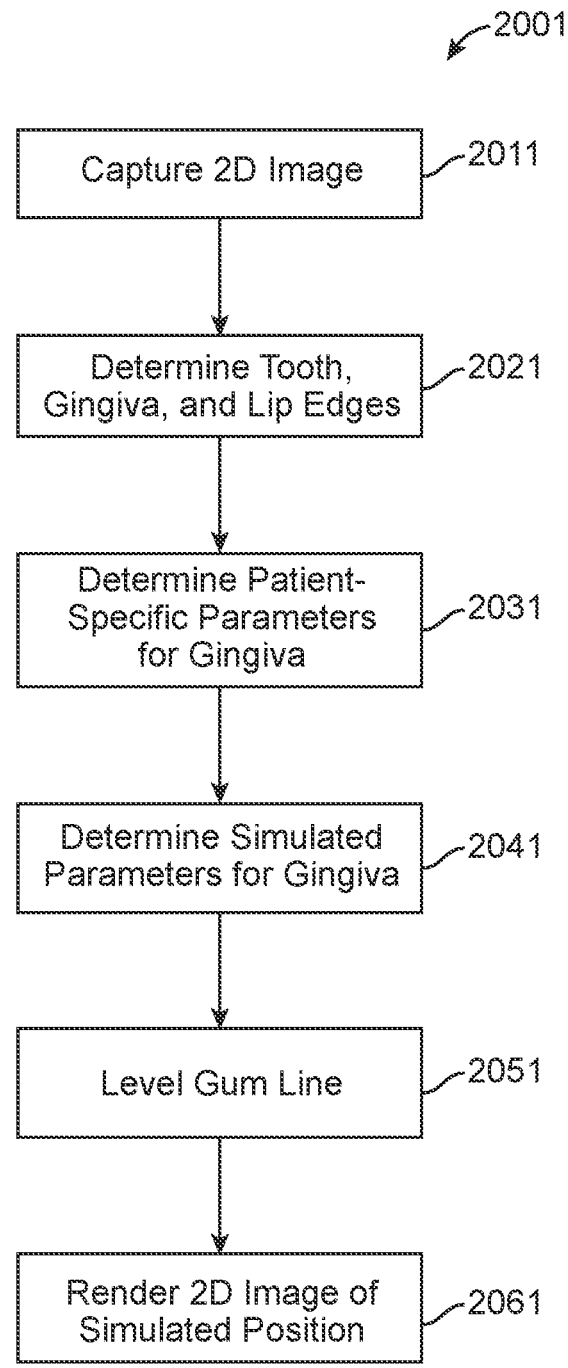
FIG. 20 illustrates a method of simulating a gingiva line, in accordance with one or more embodiments herein.

With attention to FIG. 20, a method 2001 of simulating a gingiva line using a combination of patient-specific and simulated input parameters is depicted. At block 2011, one or more 2D image(s) of a patient are captured or retrieved. The 2D images may be captured as described at block 110 of FIG. 1. One or more 2D image(s) of a patient are captured. The 2D image may depict the mouth of the patient, for example, in a smiling position. The 2D image may also be obtained as part of the processes described at block 610 of FIG. 6, block 1020 of FIG. 10A, or block 1015 of FIG. 10B. For example, the 2D image captured at block 1020 may be retrieved at block 2011 for use in generating gingiva for use in the 2D image generated at block 1050 or block 1060.

At block 2021, the edges of oral features of the patient, such as the teeth, gingiva, and lips, are determined from the 2D image of the patient's mouth. Edges of the oral features, for example, the teeth, lips, and gingiva, may be identified as described at block 620 of FIG. 6. Facial landmarks from the 2D image of the patient, may be used to identify the mouth opening, within which oral features, including the teeth and gingiva are located.

An initial determination of the edges of the oral features may be identified by a machine learning algorithm. Initial tooth contours are extracted from the image and may have a brightness or other scale applied to them. The initial contours may then undergo binerization to change the pixels of the image to a binary scale. The binarized tooth contours are thinned to, for example, a single pixel width, forming a thinned tooth contour. The initial determination of the patient's lips may be based on facial landmarks, such as the lip landmarks determined according to a machine learning algorithm, such as a convoluted neural network. As with the tooth contours, the lip contours have a brightness or other scale applied to them. The lip contours are binarized, thinned, and contoured, as with the initial tooth contours. The binarized and thinned tooth and lip contours may define the edges of the oral features. The edges may be determined for example, as described above with respect to FIG. 6.

Figure 21A:
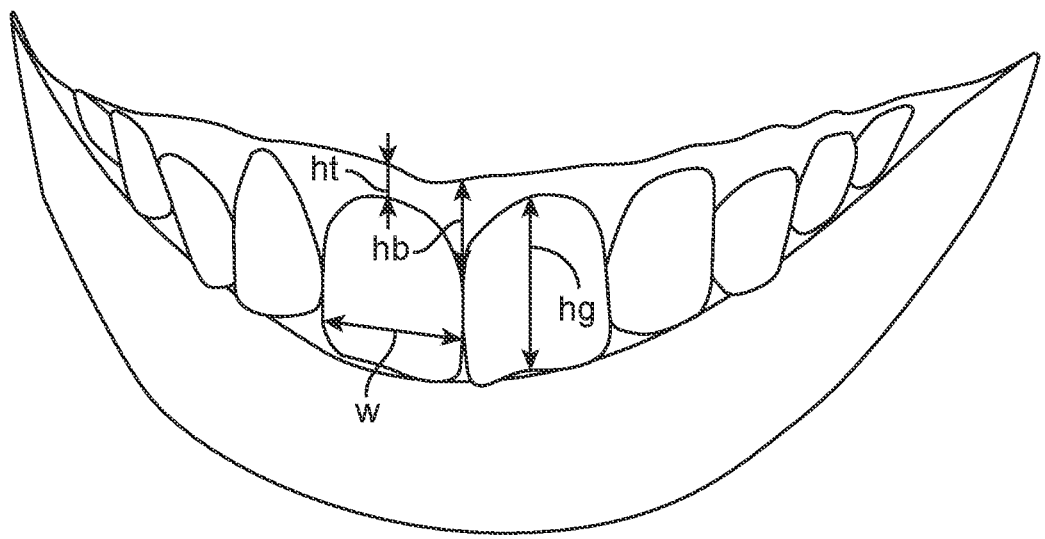
FIG. 21A illustrates gingiva line input determined from a 2D image of a patient's teeth, in accordance with one or more embodiments herein.
Figure 21B:
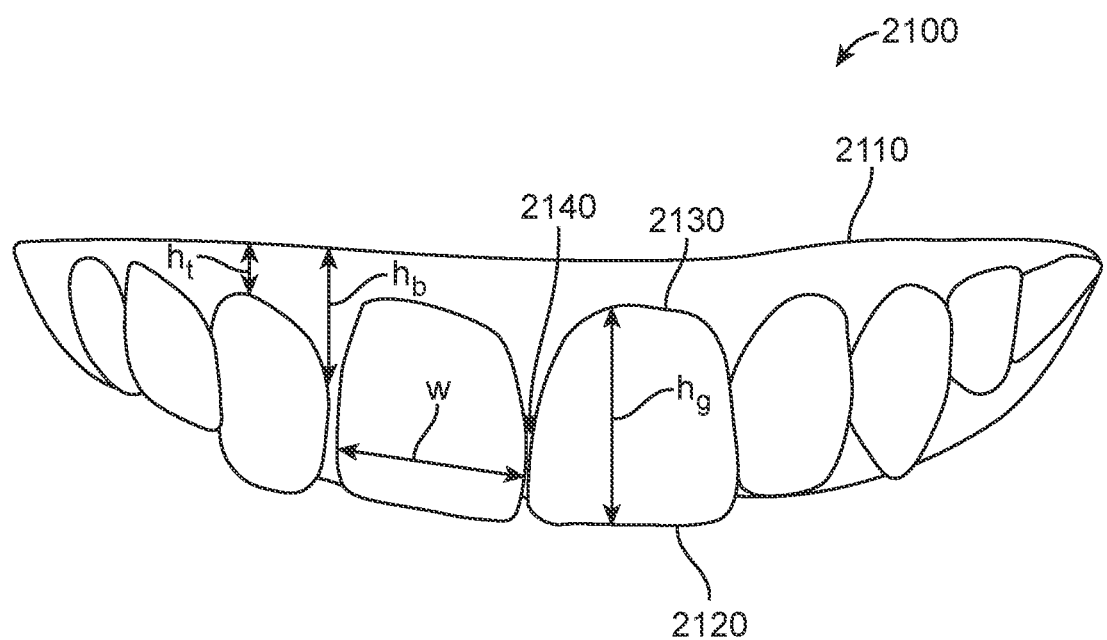
FIG. 21B depicts a process of modeling a gingiva line based on input determined from a 2D image of a patient's teeth, in accordance with one or more embodiments herein.

At block 2031, patient-specific input parameters for gingiva are determined. The input parameters may include the patient-specific input parameters shown in FIG. 21A. In some embodiments, the patient-specific input parameters may be determined by the shape and scale of one or more of the oral features of the captured 2D image of the patient. The patient-specific input parameters may be determined based on the edges of the oral features, for example, as illustrated in 2100 of FIG. 21B. The edges of the oral features may include, for example, edges of lips 2110, edges teeth 2120, and edges of gingiva 2130, determined at block 2021. The patient-specific input parameters may include a patient tooth height, which may be a distance between an incisal edge 2120 of a tooth and the edge of the gingiva 2130 or gingiva line and may be determined for each tooth of a patient's arch. The patient tooth height may be denoted by $h_g$, as shown, for example, in FIG. 21A. In some embodiments, the patient tooth height may be a maximal distance between the incisal edge 2120 of the tooth and the edge of the gingiva 2130. In some embodiments, the maximal distance may be measured as the distance between the incisal edge 2120 of the tooth and the edge of the gingiva 2130 at the gingival zenith.

In some embodiments, the patient-specific input parameters may include a gingival tip distance, which may be a distance between the edge of the lip 2110 and the gingiva line 2140. The distance may be determined at a position between each pair of neighboring teeth of the patient's arch. The gingival tip distance may be denoted by $h_b$, as shown, for example, in FIG. 21A. In some embodiments, the patient tooth height may be a maximal distance between the edge of the lip 2110 and the edge of the gingiva 2140. The maximal may be measured as the distance between the lip and the edge of the gingiva 2140 at the gingival nadir. The patient-specific input parameters may include a gingival height, which may be a distance between the edge of the lip 2110, and the gingiva line 2130, determined for each tooth of a patient's arch, the gingival height may be denoted by $h_t$, as shown, for example, in FIG. 21A. In some embodiments, the gingival height may be a minimal distance between the edge of the lip 2110 and the gingival zenith 2130. The patient-specific input parameters may include a tooth width, determined for each tooth of the patient's arch. The tooth width may be denoted by w, as shown, for example, in FIG. 21A. In some embodiments, the tooth width may be a width of a tooth at the incisal edge 2120. In some embodiments, the tooth width may be a width of a tooth at the maximal tooth width.

Figure 22:
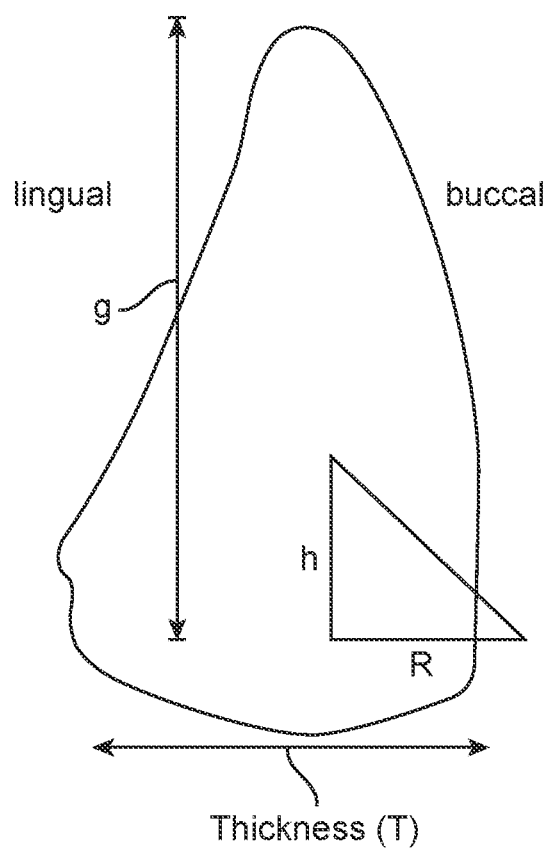
FIG. 22 illustrates gingiva line parameters, in accordance with one or more embodiments herein.

At block 2041, simulated parameters for gingiva are determined. The simulated parameters may be derived based on the patient-specific input parameters and may be used in generating the simulated gingiva. In some embodiments, the parameters of gingiva tip parameter, denoted by h, visible tooth height, denoted by g, and tooth curvature, denoted by R, may be a convolution of patient-specific input parameters, as shown in FIG. 22. For example, they may be a convolution of patient-specific parameters and simulated input parameters or ideal aesthetic parameters. An 'ideal tooth,' may include a representation of a tooth or parameters of a taken from a model arch, such as those of historical cases and/or those representing idealized arch forms. An ideal tooth may be characterized by various parameters, including, without limitation: a gingiva tip parameter, an ideal tooth height, a tooth thickness, a distance from the gingiva line to the lip, or a visible tooth height. The patients-specific parameters may be, for example, the parameters of the patient tooth height, denoted by $h_g$, the gingiva tip distance, denoted by $h_b$, the gingival height, denoted by $h_t$, and the tooth width, denoted by w, discussed above. The simulated input parameters or ideal aesthetic parameters may be, for example, the parameters of ideal tooth height, denoted by $H_g$, customizable tooth height scaling parameters denoted by $c_1$ and $c_2$, a customizable gingiva tip scaling parameter, denoted by s, and a tooth shape scaling parameter, denoted by m. The visible tooth height, denoted by g, may be a weighted average of the visible tooth height of a patient's teeth determined based on the 2D image, denoted by $h_g$, and an ideal tooth height, denoted by $H_g$. The visible tooth height, denoted by g, may be determined based on the weighted average, for example, $g=c_1 H_g + c_2 h_g$, where $c_1$ and $c_2$ are customizable tooth height scaling parameters and where $c_1+c_2=1$. For example, $c_1$ may be 0.1, 0.2, 0.3, 0.4, 0.5, 0.6, 0.7, 0.8, or 0.9. For example, $c_1$ may be from 0.1 to 0.5, 0.2 to 0.6, 0.3 to 0.7, 0.4 to 0.8, or 0.5 to 0.9. In some embodiments, $c_1$ is adjusted by a user, such as a dental professional or patient.

In some embodiments, the visible tooth height, denoted by g, represents the visible tooth height of a patient's teeth determined based on the 2D image, denoted by $h_g$. A gingiva tip parameter for each tooth, h, may be determined based on patient-specific input parameters, for example, where $h=h_b-h_t$. The gingiva tip parameter describes the shape of the gingiva surrounding a tooth. A gingiva tip parameter of 0 describes a gingiva line having a straight line across a tooth, and positive gingiva tip parameter describes a gingiva line having an curved shape where the distance between the lip and the gingiva line is greater between two teeth than at the midline of a tooth. In some embodiments, the gingiva tip parameter, h, may be determined based the difference between the patient-specific tooth height, denoted by $h_g$, the ideal tooth height, denoted by $H_g$, and a customizable gingiva tip scaling parameter, denoted by s, for example, where $h=s(H_g-h_g)(h_b-h_t)$ with s determined by the difference between $H_g$ and $h_g$. For example when the difference is large, it is likely to have long squared teeth, s then takes a larger value; when the difference is small, s takes a relatively small value. In some embodiments, s may be adjusted based on the difference of ideal tooth length $H_g$ and the patient's tooth length $h_g$. For example, s may be 0.8, 0.9, 1.0, 1.1, 1.2, 1.3, 1.4, 1.5, 1.6, 1.7, 1.8, 1.9, or 2.0. For example, s may be varied from 0.8 to 1.0, 0.9 to 1.1, 1.0 to 1.2, 1.1 to 1.3, 1.2 to 1.4, 1.3 to 1.5, 1.4 to 1.6, 1.5 to 1.7, 1.6 to 1.8, 1.7 to 1.9, 1.8 to 2.0, or 0.8 to 2.0. In some embodiments, s is adjusted by a user, such as a dental professional or patient.

A maximum threshold for the gingiva tip parameter, denoted by h, for each tooth may be set as a fraction of patient tooth height, denoted by $h_g$. For example, the gingiva tip parameter, h, may be set so as not to exceed $0.2h_g$, $0.3h_g$, $0.4h_g$, $0.5h_g$, $0.6h_g$, $0.7h_g$, $0.75h_g$, $0.8h_g$, $0.85h_g$, or $0.9h_g$.

The maximum threshold for the gingiva tip parameter, h, may be set as a fraction of visible tooth height, denoted by g. For example, h may not exceed 0.2 g, 0.3 g, 0.4 g, 0.5 g, 0.6 g, 0.7 g, 0.75 g, 0.8 g, 0.85 g, or 0.9 g.

The tooth curvature parameter, denoted by R, may be a function of the patient-specific gingiva width parameter, denoted by $h_r$, tooth thickness, denoted by T, and a tooth shape scaling parameter, denoted by m. In some embodiments, the tooth curvature parameter, R, may be determined by $R=mh_rT$. In some embodiments, the tooth thickness, denoted by T, may be determined based on the parameterized 3D model of the patient's teeth, for example, where T is the distance between a lingual surface and a buccal surface of a tooth at the midpoint of the gingiva line. In some embodiments, m is adjusted based on the patient's tooth length, denoted by $h_g$. For example, m may be 0.1, 0.2, 0.3, 0.4, 0.5, 0.6, 0.7, 0.8, 0.9, 1.0. For example, m may be varied from 0.1 to 0.3, 0.2 to 0.4, 0.3 to 0.5, 0.4 to 0.6, 0.5 to 0.7, 0.6 to 0.8, 0.7 to 0.9, or 0.8 to 1.0. In some embodiments, m is adjusted by a user, such as a dental professional or patient.

In some embodiments, the input parameters, for example the parameters denoted by h, g, and R, are used to determine a parameterized gingiva line. The patient-specific input parameters, the convolution of the patient-specific input parameters, and the simulated input parameters, or any combination thereof may be used to determine the gingiva line. In some embodiments, determining the parameterized gingiva line comprises approximating the parametric 3D model of a tooth of the patient's teeth as a cylinder. The cylinder may be cut cross-sectionally by a tilted plane, wherein the orientation and location of the tilted plane is determined based on the input parameters such that the line of intersection between the tilted plane and the cylinder passes through the coordinates defined by h, g, and R. The line of intersection between the tilted plane and the cylinder may be used to define the edge of the gingiva. In some embodiments, determining the parameterized gingiva line comprises cutting the 3D model of the patient's teeth cross-sectionally by a tilted plane, wherein the orientation and location of the tilted plane is determined based on the input parameters such that the line of intersection between the tilted plane and the cylinder passes through the coordinates defined by h, g, and R. The line of intersection between the tilted plane and the 3D model of the patient's teeth may be used to define the edge of the gingiva. Points on the gingival side of the line of intersection between the tilted plane and the cylinder or the 3D model of the patient's teeth are rendered as gingiva, while points of on the incisal side of the line of intersection between the tilted plane and the cylinder are rendered as teeth. In some embodiments, the points are a 3D point cloud of points. In some embodiments, points are pixels of a 2D image.

Figure 23:
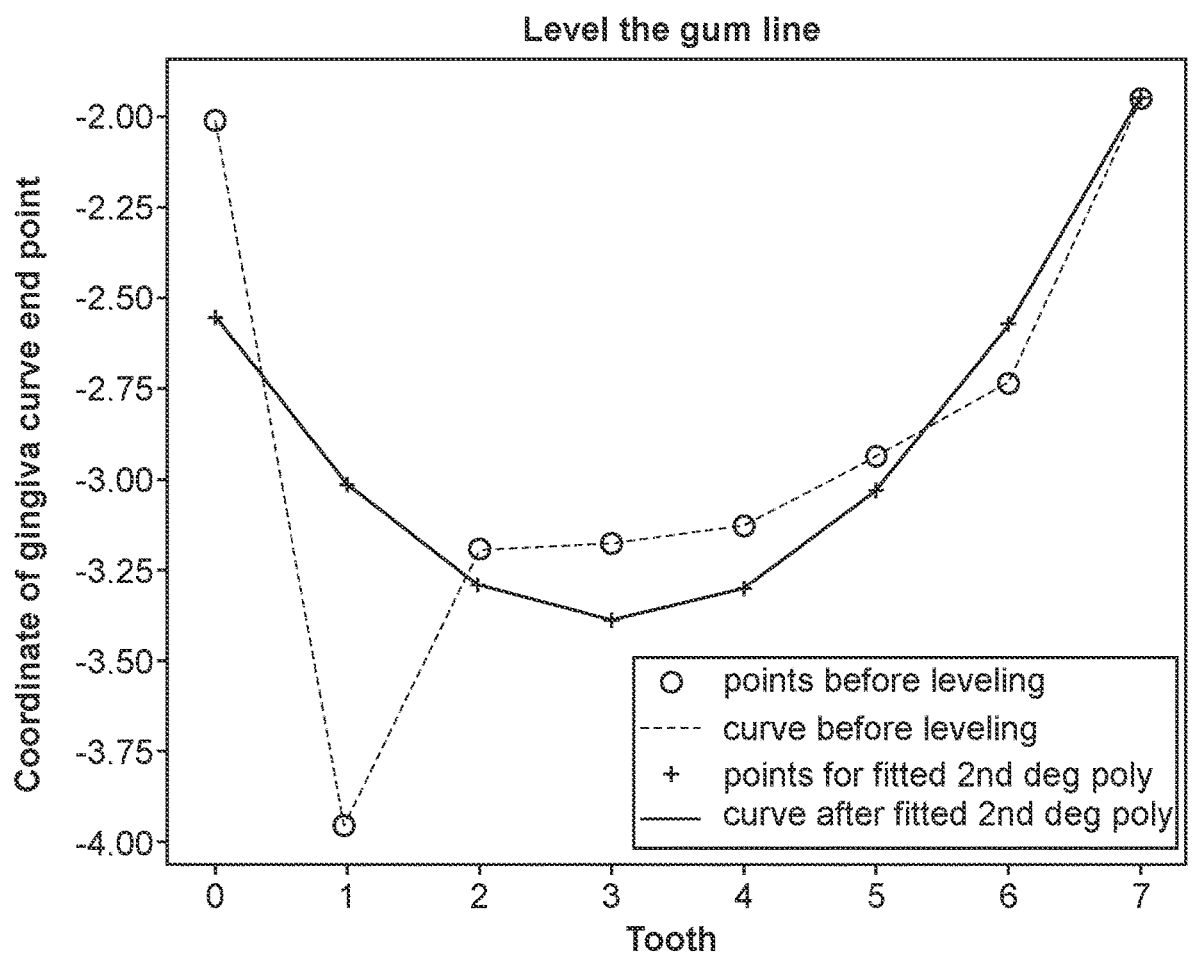
FIG. 23 illustrates a method of leveling a gingiva line, in accordance with one or more embodiments herein.

At block 2051, the gum line is optionally leveled. The gum line, which intersects corresponding coordinates of the gingiva line of each tooth, may be adjusted by fitting to a second degree polynomial as shown in FIG. 23. The gum line may be adjusted such that corresponding coordinates of the gingiva line are positioned along the line defined by the second degree polynomial fit. In some embodiments, the corresponding coordinates of each tooth are the gingiva curve end points, or gingiva zenith 2130 in FIG. 21B, the point on the gingiva line of a tooth at which the distance between the gingiva line and the lip is the shortest. In some embodiments, the corresponding coordinates of each tooth are the gingiva curve tip points, or gingiva nadir 2140 in FIG. 21B, the point on the gingiva line between two teeth at which the distance between the gingiva line and the lip is the longest.

The gingiva line determined based on the patient-specific and simulated input parameters as described in method 2001 and, optionally, leveled as described in FIG. 23, may be used to render the gingiva in the final 2D image of the patient's teeth either in the initial position or in the final position following simulated treatment as described at block 140 of FIG. 1, block 650 of FIG. 6, block 1060 of FIG. 10A, or block 1055 of FIG. 10B.

The result of the parameterized gingiva line simulation using a combination of the patient-specific parameters, simulated parameters, and ideal aesthetic parameters, illustrated in FIG. 20 and, optionally, gum line leveling, illustrated in FIG. 23, is a gingiva line in the rendered 2D image that more closely matches the initial captured 2D image and produces a more aesthetically correct simulated 2D image than a parameterized gingiva line defined entirely by patient-specific input parameters. This improvement may be more apparent in cases where the lip covers part of one or more teeth, one or more teeth are chipped or damaged, one or more teeth are crooked, or the patient's width-height tooth ratio deviates substantially from an ideal width-height tooth ratio. Additionally, the parameterized gingiva line simulation is less computationally intensive than generating a 3D gum model using a 3D mesh template.

At block 2061, the simulated position of the parameterized gingiva line and 3D tooth model in either the initial position or the final matched position are rendered and inserted into the 2D image of the patient. Rendering of the 2D image is described in more detail at block 1060 of FIG. 10A. The 3D rendering of the teeth may be placed in the mouth of the patient as defined by the lip contours. An image of the parameterized gingiva line identified in method 2001 of FIG. 20 may be also rendered in the 2D image.

In some embodiments, neural networks, such as generative adversarial networks or conditional generative adversarial networks may be used to integrate a 3D model of teeth in a final position with a facial image of a patient and match the colors, tones, shading, and other aspects of the 3D model with a facial photo. The neural network is trained using facial images. In some embodiments, the facial images may include images of people's faces having a social smiles. In some embodiments, the facial images may include facial images of patient's teeth before orthodontic treatment. During training, patient's teeth and their contours may be identified. For example, each tooth may be identified by type (e.g., upper left central incisor, lower right canine). Other aspects and features of the image may also be identified during training, such as the location and color of the gingiva, the color of the teeth, the relative brightness of the surfaces within the mouth, and others.

Referencing FIG. 24, after training, the neural network receives inputs at block 4804 for use in generating a realistic rendering of the patient's teeth in a clinical final position. In some embodiments, the inputs may include one or more of an image of a rendering of a 3D model of the patient's teeth in a clinical final position or a 3D rendered model of the patients teeth in the clinical final position 4808, the clinical final position determined, for example, according to an orthodontic treatment plan, the parameterized gingiva line, a blurred initial image of the patient's teeth 4810, and a color coded image 4812 of the 3D model of the patient's teeth in the clinical final position.

The image of a rendering of a 3D model of the patient's teeth in a clinical final position or the 3D rendered model of the patient's teeth in the clinical final position 4808 may be determined based on the clinical orthodontic treatment plan for moving the patient's teeth from the initial position towards the final position, as described above. The image or rendering 4808 may be generated based on the imaging perspectives. For example, one or more of the imaging distance, the focal length of the imaging system, and the size of the patient's teeth in the initial facial image may be used to generate the image or rendering.

The blurred image of the patient's teeth 4810 may be generated using one or more blur algorithms, such as a Gaussian blur algorithm. In some embodiments, the Gaussian blur may have a large radius, for example, a radius of at least 5, 10, 20, 40, or 50 pixels. In some embodiments, the blur is sufficiently large such that the tooth structure is not discernable in the blurred image.

The coded model of the patient's teeth 4812 may be a red-green-blue (RGB) color coded image of a model of the patient's teeth, with each color channel corresponding to a different quality or feature of the model. For example, the green color channel, which may be an 8-bit color channel indicates the brightness of the blurred image 4810 on a scale of 0 to 255 as, for example, overlaid on the 3D model.

The red color channel may be used to differentiate each tooth and the gingiva from each other. In such an embodiment, the gingiva 4813 may have a red channel value of 1, the left upper central incisor 4814 may have a red value of 2, the right lower canine may have a red channel of 3, the portions of the model that are not teeth or gingiva might have a red channel value of 0, and so on, so that the red channel value of each pixel identifies the dental anatomy associated with the pixel.

The blue color channel may be used to identify the angle of the teeth and/or gingiva with respect to the facial plane. For example, at each pixel location the angle normal to the surface of the dental structure, is determined and a value between 0-255 (for 8-bit color channels) is assigned to the pixel. Such information allows the neural network to, for example, model light reflectivity from the dental surfaces.

The neural network then uses the inputs and its training to render a realistic image 4806 of the patient's teeth in a final position. This realistic image is then integrated into the mouth opening of the facial image and an alpha channel blurring is applied.

Figure 12:
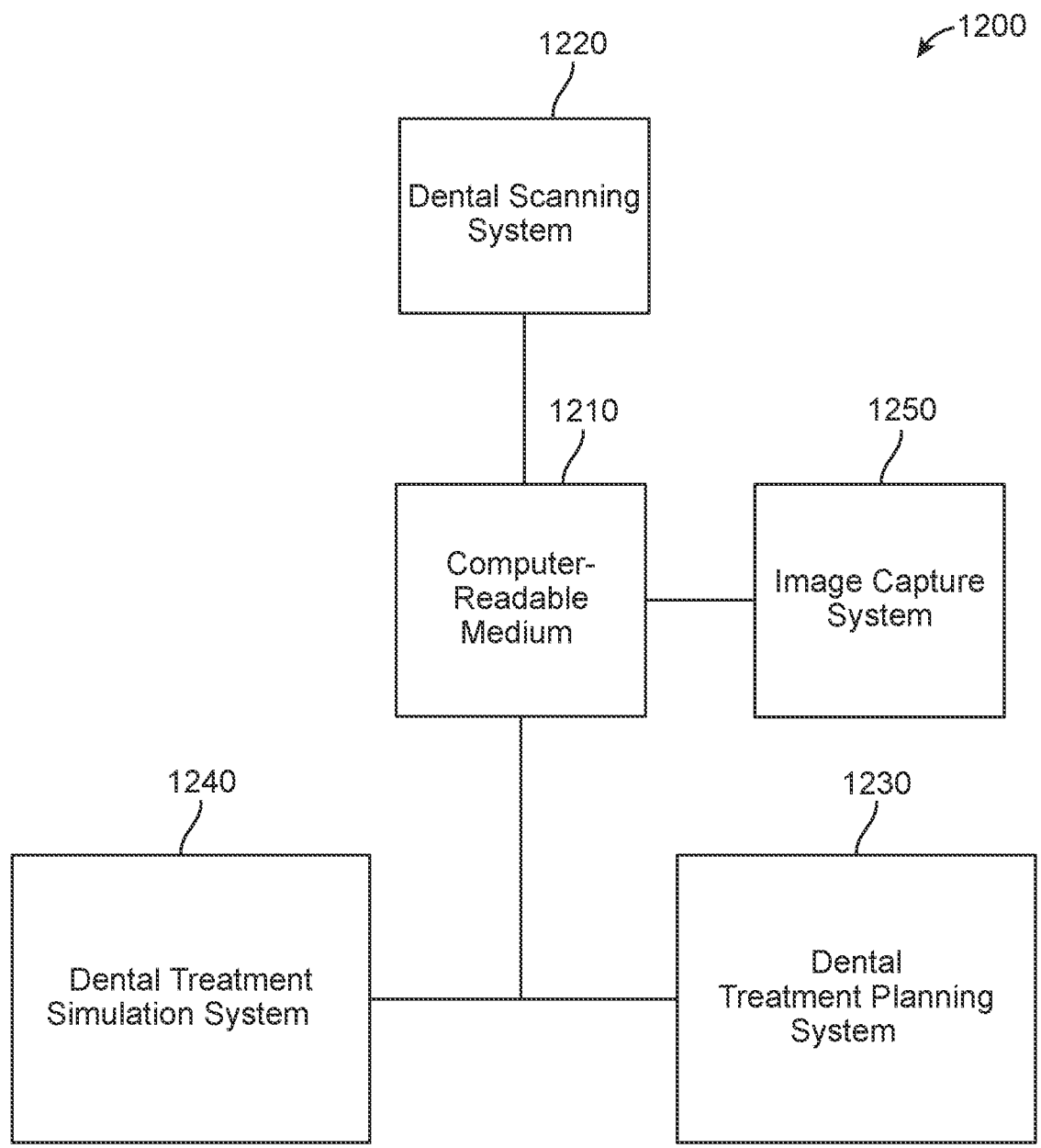
FIG. 12 depicts a system for simulating an estimated outcome of an orthodontic treatment, in accordance with one or more embodiments herein.

FIG. 12 depicts a system 1200 for simulating an estimated and/or intended outcome of an orthodontic treatment, in accordance with some embodiments. In the example of FIG. 12, the system 1200 includes a computer-readable medium 1210, a dental scanning system 1220, dental treatment planning system 1230, a dental treatment simulation system 1240, and an image capture system 1250. One or more of the elements of the system 1200 may include elements of such as those described with reference to the computer system shown in FIG. 20. One or more elements of the system 1200 may also include one or more computer-readable media including instructions that when executed by a processor, for example, a processor of any of the systems 1220, 1230, 1240, and 1250 cause the respective system or systems to perform the processes described herein.

The dental scanning system 1220 may include a computer system configured to capture one or more scans of a patient's dentition. The dental scanning system 1220 may include a scan engine for capturing 2D images of a patient. Such images may include images of the patient's teeth, face, and jaw. The images may also include x-rays or other subsurface images of the patient. The scan engine may also capture 3D data representing the patient's teeth, face, gingiva, or other aspects of the patient.

The dental scanning system 1220 may also include a 2D imaging system, such as a still or video camera, an x-ray machine, or other 2D imager. In some embodiments, the dental scanning system 1220 also includes a 3D imager, such as an intraoral scanner or an impression scanner. The dental scanning system 1220 and associated engines and imagers can be used to capture the historic scan data for use in determining the historic mean parameters of a 3D parametric dental model, as described with reference to FIGS. 1-11 herein. The dental scanning system 1220 and associated engines and imagers can be used to capture the 2D images of a patient's face and dentition for use in building a 3D parametric model of the patient's teeth, as described for example, with reference to FIGS. 1-11 herein.

The dental treatment simulation system 1240 may include a computer system configured to simulate one or more estimated and/or intended outcomes of a dental treatment plan. In some implementations, the dental treatment simulation system 1240 obtains photos and/or other 2D images of a consumer/patient. The dental treatment simulation system 1240 may further be configured to determine tooth, lip, gingiva, and/or other edges related to teeth in the 2D image. As noted herein, the dental treatment simulation system 1240 may be configured to match tooth and/or arch parameters to tooth, lip, gingiva, and/or other edges. The dental treatment simulation system 1240 may also render a 3D tooth model of the patient's teeth. The dental treatment simulation system 1240 may gather information related to historical and/or idealized arches representing an estimated outcome of treatment. The dental treatment simulation system 1240 may, in various implementations, insert, align, etc., the 3D tooth model with the 2d image of the patient in order to render a 2D simulation of an estimated outcome of orthodontic treatment. The dental treatment simulation system 1240 may include a photo parameterization engine which may further include an edge analysis engine, an EM analysis engine, a course tooth alignment engine, and a 3D parameterization conversion engine. The dental treatment simulation system 1240 may also include a parametric treatment prediction engine which may further include a treatment parameterization engine, a scanned tooth normalization engine, and a treatment plan remodeling engine. The dental treatment simulation system 1240 and its associated engines may carry out the processes described above with respect to FIGS. 5-9.

The dental treatment planning system 1230 may include a computer system configured to implement treatment plans. The dental treatment planning system 1230 may include a rendering engine and interface for visualizing or otherwise displaying the simulated outcome of the dental treatment plan. For example, the rendering engine may render the visualizations of the 3D models described herein, for example, at block 140 of FIG. 1, at blocks 640, 650, and 660 of FIG. 6, process 800, described with reference to FIG. 8, at blocks 910, 920, and 930 of FIG. 9, block 1150 of FIG. 10, block 1150 of FIG. 11, and block 2061 of FIG. 20. The rendering engine may render the realistic rendering of the patient's teeth in a clinical final position, described with reference to FIG. 24. The dental treatment planning system 1230 may also determine an orthodontic treatment plan for moving a patient's teeth from an initial position, for example, based in part on the 2D image of the patient's teeth, to a final position. The dental treatment planning system 1230 may be operative to provide for image viewing and manipulation such that rendered images may be scrollable, pivotable, zoomable, and interactive. The dental treatment planning system 1230 may include graphics rendering hardware, one or more displays, and one or more input devices. Some or all of the dental treatment planning system 1230 may be implemented on a personal computing device such as a desktop computing device or a handheld device, such as a mobile phone. In some embodiments, at least a portion of the dental treatment planning system 1230 may be implemented on a scanning system, such as the dental scanning system 1220. The image capture system 1250 may include a device configured to obtain an image, including an image of a patient. The image capture system may comprise any type of mobile device (iOS devices, iPhones, iPads, iPods, etc., Android devices, portable devices, tablets), PCs, cameras (DSLR cameras, film cameras, video cameras, still cameras, etc.). In some implementations, the image capture system 1250 comprises a set of stored images, such as images stored on a storage device, a network location, a social media website, etc.

Figure 13:
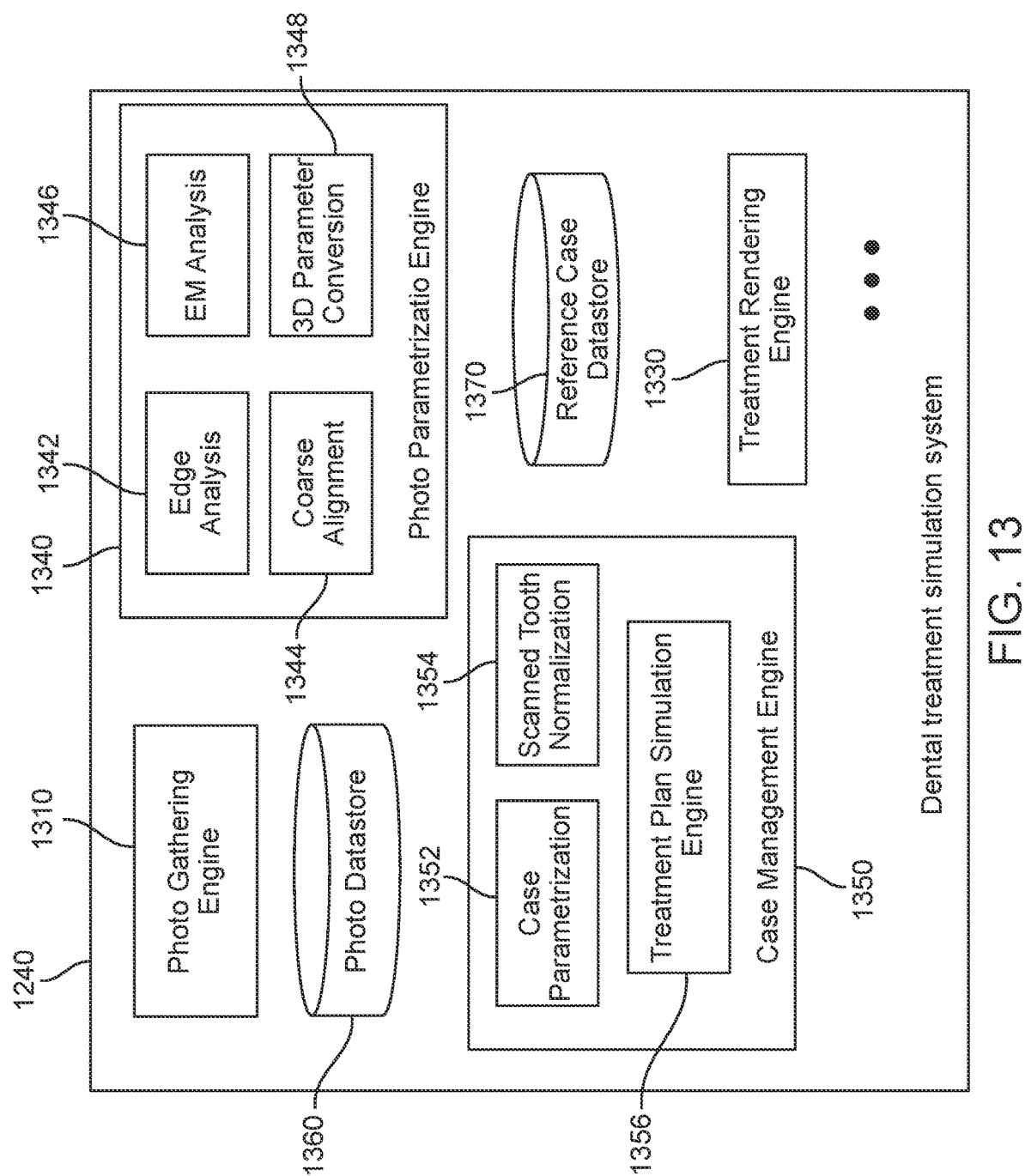
FIG. 13 depicts an example of one or more of the elements of the estimated orthodontic treatment simulation system, in accordance with one or more embodiments herein.

FIG. 13 shows an example of one or more of the elements of the dental treatment simulation system 1240, in accordance with some embodiments. In the example of FIG. 13, the dental treatment simulation system 1240 includes a photo gathering engine 1310, a photo datastore 1360, a photo parameterization engine 1340, a case management engine 1350, a reference case datastore 1370, and a treatment rendering engine 1330.

The photo gathering engine 1310 may implement one or more automated agents configured to retrieve a selected photo of a patient from the photo datastore 1360, the image capture system 1250, and/or a scan from the dental scanning system 1220. The photo gathering engine may then provide the photo or photos to the photo parameterization engine 1340. The photo gathering engine may then provide the photo or photos to the photo parameterization engine 1340 and/or other modules of the system.

The photo datastore 1360 may include a datastore configured to store photos of patients, such as their facial photos. In some embodiments, the photos are 2D images that include the mouth of the patient and one or more images of the face, head, neck, shoulders, torso, or the entire patient. The 2D image of the patient may include an image of the patient with their mouth in one or more positions; for example, the patient's mouth may be a smiling position, such as a social smiling position, a repose position with relaxed muscles and lips slightly parted, or anterior retracted open bite or closed bite positions. In some embodiments the image of the patient is taken with an image capture system. The image may be captured with a lens at a predetermined focal length and at a distance from the patient. The image may be captured remotely and then received for processing. The image may be a series of images of video captured from one or more perspectives. For example, the images may include one or more of a frontal facial image and a profile image, including one or more three-quarter profile images and full profile images.

The photo parameterization engine 1340 may implement one or more automated agents configured to build a parametric 3D model based on the 2D image of the patient from the photo datastore 1360 and the parametric model and mean data from the parametric treatment prediction engine. The edge analysis engine 1342 may implement one or more automated agents configured to determine the edges of the teeth, lips and gingiva within the photo of the patient. For example as described with respect to FIG. 6. In particular, an initial determination of the patient's lips (for example, the inner edges of the lips that define the mount opening), teeth, and gingiva contours may be identified by a machine learning algorithm, such as a convoluted neural network.

Then, the initial contours may be extracted from the image. The pixels that denote the contours may then undergo binarization. The binarized tooth contours are thinned, whereby the contour's thickness is reduced to, for example, a single pixel in width, forming a thinned contour.

Using the contours, either thinned or otherwise, parameterized 3D teeth and arch models are matched to each of the patient's teeth that are depicted in the 2D image of the patient. The matching is based on the contours, determined above.

The coarse alignment engine 1344 may implement one or more automated agents configured to receive the 2D image and/or the associated edges and performs a coarse alignment between the identified edges and the mean tooth models, for example, as described with reference to FIG. 7A, wherein the respective centers of the teeth in the 2D image and the silhouette of the parametric tooth may be aligned before the 2D image and/or associated edges, along with the silhouettes and their associated tooth parameters are sent to the EM engine 1346.

The expectation maximization (EM) engine 1346 may implement one or more automated agents configured to perform an expectation-maximization analysis between the edges of the 2D image and the parameters of the 3D parametric model, for example as described with respect to FIG. 7A, and in particular, blocks 720, 730, and 740.

Once the EM analysis engine 1346 completes the matching of the parametric 3D model to the 2D image of the patient, the parametric results are sent to the 3D parameter conversion engine 1348, which may convert the output principle component analysis of the EM analysis engine to case-specific parameters that define a 3D model of the patient's teeth according to a parametric model for use by the parametric treatment prediction engine 1350, as described above.

The gingiva parameterization engine 1345 may implement one or more automated agents configured to build a gingiva line model based on patient-specific input parameters and, optionally, simulated input parameters, as described with respect to FIG. 20, and in particular, blocks 2031 and 2041. The gingiva line model is generated using input from the initial 2D image of the patient's teeth, the 3D parametric model of the patient's teeth, and, optionally, ideal tooth shape parameters. The gingiva line model may then be rendered into the 2D image using the treatment rendering engine, as described at block 1330.

The gum line leveling engine 1347 may implement one or more automated agents configured to level the gum line based on gingiva line parameters generated at block 1345, the gingiva parameterization engine. Gum line leveling is, optionally, performed as described with respect to FIG. 20, and in particular, block 2051. The leveled gum line may then be rendered into the 2D image using the treatment rendering engine, as described at block 1330.

The case management engine 1350 may include a case parameterization engine 1352, a scanned tooth normalization engine 1354, and a treatment plan simulation engine 1356. The case management engine 1350 may implement one or more automated agents configured to define the parametric model used to represent the teeth and arch of patients, determine the mean data to parametrically represent the mean positions of a patient's teeth and arch based on the treatment plans retrieved from the treatment plan datastore 1370, and simulate the treatment of a particular patient's teeth based on the parametric model, the mean tooth positions, and a patient's particular teeth.

The case parameterization engine 1352 may implement one or more automated agents configured to define the parametric 3D model for use in modeling teeth. For example, the parametric 3D model may be defined as described above with reference to eq. (2). More than just defining the equation, treatment parameterization engine 1352 may also define the schema for the parameters. For example, the $T_\tau$, which represents tooth positions, may be defined as a 4*4 matrix including tooth position and rotation in 3 axis. Similarly, $a_\tau^i$, which represents tooth shape, may be defined as an 2500*3 matrix, where each vertex of the sphere is mapped to a location on the surface of the tooth model, each location of a vertex being x, y, and z special locations. For lower or higher definition models, fewer or greater vertices may be used. Further discussion of the parameters defined by the treatment parameterization engine 1352 are descried elsewhere herein, for example with respect to FIGS. 2-5.

The scanned tooth normalization engine 1354 may implement one or more automated agents configured to parameterize the scanned teeth of a set of treatment plans gathered from the treatment plan datastore 1370 and then determines the mean set of general generic parameters for the parametric model. The scanned tooth normalization engine 1354 may carry out process 350, as described with reference to FIG. 3B. For example, the scanned tooth normalization engine 1354 may align the arches within the historic cases retrieved from the datastore 1370. Each arch in the datastore is aligned at three locations: between the central incisors and at each distal end of the left and right side of each arch. Each tooth's position and orientation is then determined based on its location and orientation with reference to the alignment points.

The scanned tooth normalization engine 1354 may implement one or more automated agents configured to determine the distributions of the parameters among the cases. For example, each historic arch may be rescaled to determine Φ, then each arch is averaged to determine $T_\tau^C$, then the individual tooth local transformations are determined and compared to $T_\tau^C$ to determine $T_\tau$, then after aligning each tooth $\beta_\tau$ is determined.

From this data, each tooth's relative shape, location, and rotation are determined in order to build the distribution for each case-specific parameter. For example the distribution of the $a_\tau^i$, the coefficients for the principal components, for the surface model of the each respective tooth in all of the retrieved models is determined.

The location and orientation of each tooth is averaged to determine a mean location for each tooth and the orientation of each tooth is averaged to determine a mean orientation for each tooth. The mean location and orientation are used to determine $T_\tau^C$.

In some embodiments, the scanned teeth of a set of treatment plans gathered from the treatment plan datastore can be used to generate a template datastore of parameterized template models. The scanned tooth normalization engine 1354 may align the arches within the historic cases retrieved from the reference case datastore 1370. Each arch in the reference case datastore is aligned at three locations: between the central incisors and at each distal end of the left and right side of each arch. Each tooth's position and orientation is then determined based on its location and orientation with reference to the alignment points. The parameters of the parameterized template models in the datastore are searchable. The datastore can be used to match patient 3D models (e.g., generated from 2D models or from 3D scans) to the closest template in the datastore based on tooth shape and arch shape to identify a matched template model. The closest matched template model can be used to determine the final tooth positions and orientations for the patient's teeth.

The treatment plan simulation engine 1356 may implement one or more automated agents configured to use the parametric model defined by the treatment parametrization engine 1352, the generic parameters from the scanned tooth normalization engine and the case-specific parameters from the photo parameterization engine 1340 to simulate an estimated and/or intended outcome of a dental treatment plan of a specific patient's teeth, for example, as described with respect to FIGS. 10 and 11.

The treatment plan simulation engine 1356 retrieves or otherwise determines the mean shape, $S_\tau^C$. In some embodiments, the mean shape may be retrieved from scanned tooth normalization engine 1354. In some embodiments, the mean shape may be loaded into memory or retrieved from memory. The mean shape may also be initialized as a set of matrices, one for each tooth.

The treatment plan simulation engine 1356 performed a principal component analysis shape adjustment on the mean shape of the teeth, $S_\tau^C$. For each tooth in the model, the case specific coefficients as determined from the photo parametrization engine 1340 for the principal component, $a_\tau^i$, are applied to the principal component, $B_\tau^i$. After the shape adjustment is completed, in some embodiments, the adjusted shape may be rendered, for example, on a screen for viewing by a patient or dental professional. In some embodiments, the adjusted shape may be stored into memory. The adjusted shape may also be stored as a set of matrices, one for each tooth.

The treatment plan simulation engine 1356 determines the mean tooth pose. In some embodiments, the mean tooth pose may be based on the mean tooth pose of a set of scanned arches, as discussed above. In some embodiments, each adjusted tooth is placed in its corresponding mean location and orientation, as determined by the mean arch. In some embodiments, the mean tooth pose may be rendered, for example, on a screen for viewing by a patient or dental professional. In some embodiments, the mean tooth pose may be loaded into memory or retrieved from memory. The mean tooth pose may also be initialized as a set of matrices, one for each tooth in the tooth pose.

In some embodiments, the treatment plan remodeling engine 1356 uses the tooth position and orientation coordinates from the ideal parameterized datastore match and applies the shape and textures of the patient's 3D model generated from the 2D image to the tooth positions and orientations to generate an arch.

The treatment plan simulation engine 1356 scales the arch such that it is generated according to the patient's tooth and arch size. In some embodiments, the arch scaling factor t is based on the particular tooth and arch of a particular patient, as discussed above. In some embodiments, the arch is adjusted such that the scaled arch matches the size of a patient's arch, as determined, for example, by size of the teeth and arch in the patient's scanned arch, or otherwise, as discussed herein. In some embodiments, the scaled arch may be rendered, for example, on a screen for viewing by a patient or dental professional. In some embodiments, the scaled arch may be stored in memory. The scaled arch may also be stored as a set of matrices, one for each tooth in the tooth pose. The scaled arch may be sent to the treatment rendering engine 1330.

The treatment rendering engine 1330 renders the teeth and 2D image of the patient in a final position, as determined, for example, by the parametric treatment prediction engine 1350 and, in particular, the treatment plan simulation engine 1356 therein. The treatment rendering engine 1330 may carry out some of the processes described with reference to FIGS. 9, 10, and 11. In particular, the rendering processes descried with reference to FIGS. 9, 10, 11, and elsewhere herein.

Figure 14:
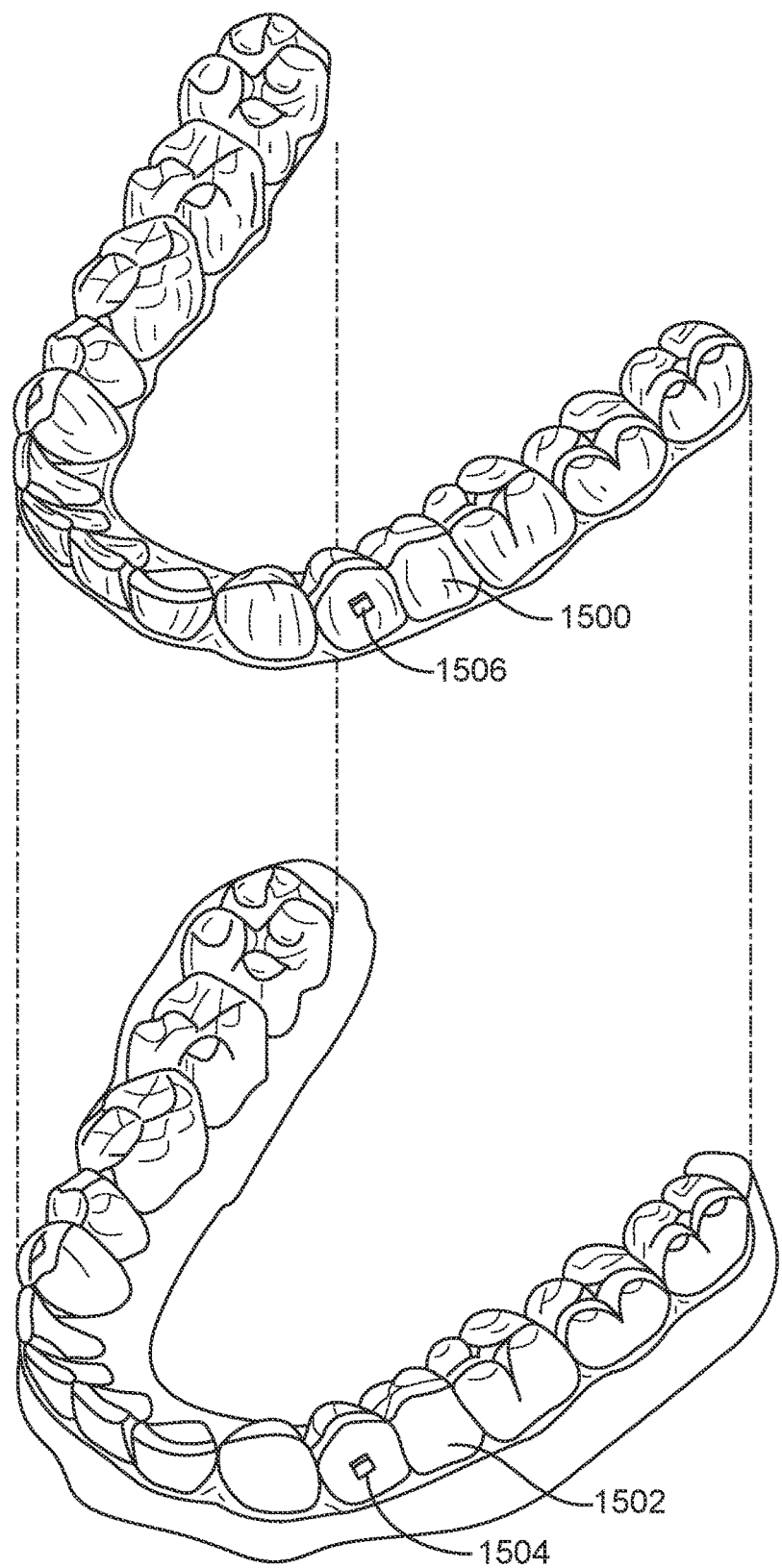
FIG. 14 illustrates a tooth repositioning appliance, in accordance with one or more embodiments herein.

FIG. 14 illustrates an exemplary tooth repositioning appliance or aligner 1500 that can be worn by a patient in order to achieve an incremental repositioning of individual teeth 1502 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient. In some embodiments, no wires or other means will be provided for holding an appliance in place over the teeth. In some cases, however, it may be desirable or necessary to provide individual attachments or other anchoring elements 1504 on teeth 1502 with corresponding receptacles or apertures 1506 in the appliance 1500 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

Figure 15:
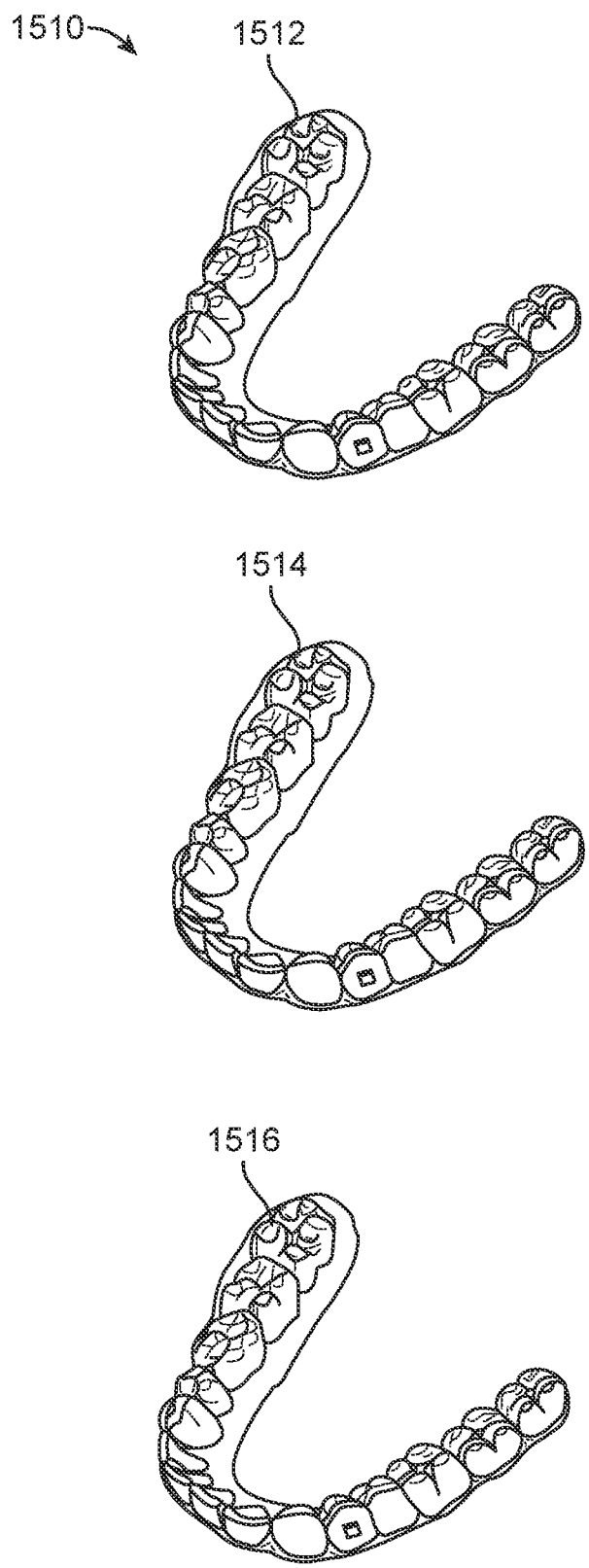
FIG. 15 illustrates a tooth repositioning system, in accordance with one or more embodiments herein.

FIG. 15 illustrates a tooth repositioning system 1510 including a plurality of appliances 1512, 1514, 1516. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement towards a target tooth arrangement by placing a series of incremental position adjustment appliances over the patient's teeth. For example, the tooth repositioning system 1510 can include a first appliance 1512 corresponding to an initial tooth arrangement, one or more intermediate appliances 1514 corresponding to one or more intermediate arrangements, and a final appliance 1516 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 16:
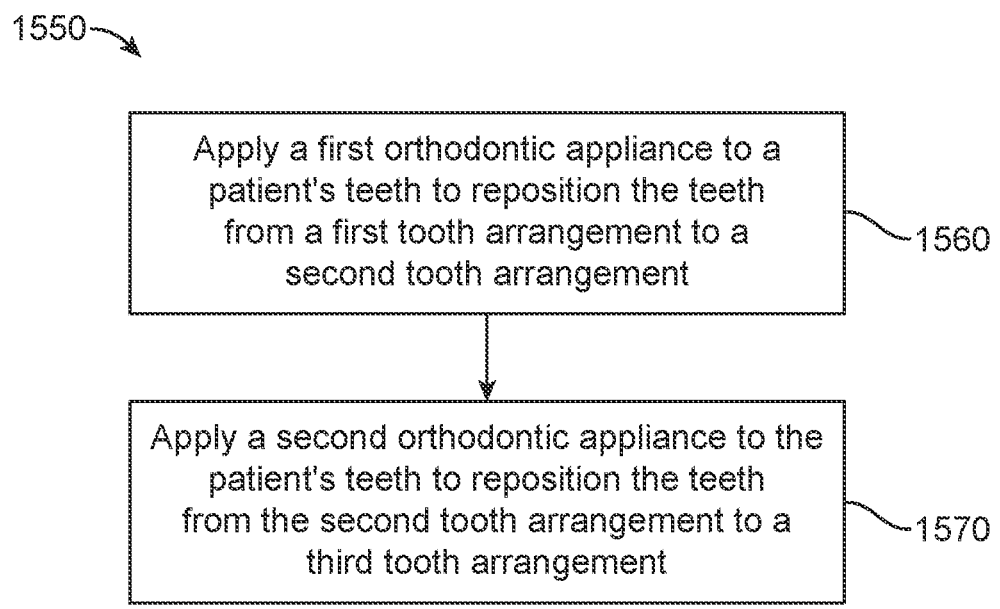
FIG. 16 illustrates a method of orthodontic treatment using a plurality of appliances, in accordance with one or more embodiments herein.

FIG. 16 illustrates a method 1550 of orthodontic treatment using a plurality of appliances, in accordance with embodiments. The method 1550 can be practiced using any of the appliances or appliance sets described herein. In block 1560, a first orthodontic appliance is applied to a patient's teeth in order to reposition the teeth from a first tooth arrangement to a second tooth arrangement. In block 1570, a second orthodontic appliance is applied to the patient's teeth in order to reposition the teeth from the second tooth arrangement to a third tooth arrangement. The method 1550 can be repeated as necessary using any suitable number and combination of sequential appliances in order to incrementally reposition the patient's teeth from an initial arrangement to a target arrangement. The appliances can be generated all at the same stage or in sets or batches (at the beginning of a stage of the treatment, at an intermediate stage of treatment, etc.), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry.

In some embodiments, the orthodontic appliances herein can be fabricated using a combination of direct and indirect fabrication techniques, such that different portions of an appliance can be fabricated using different fabrication techniques and assembled in order to form the final appliance. For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). The computer-based methods presented herein can improve the accuracy, flexibility, and convenience of appliance fabrication.

In some embodiments, computer-based 3D planning/design tools, such as Treat™ software from Align Technology, Inc., may be used to design and fabricate the orthodontic appliances described herein.

Figure 17:
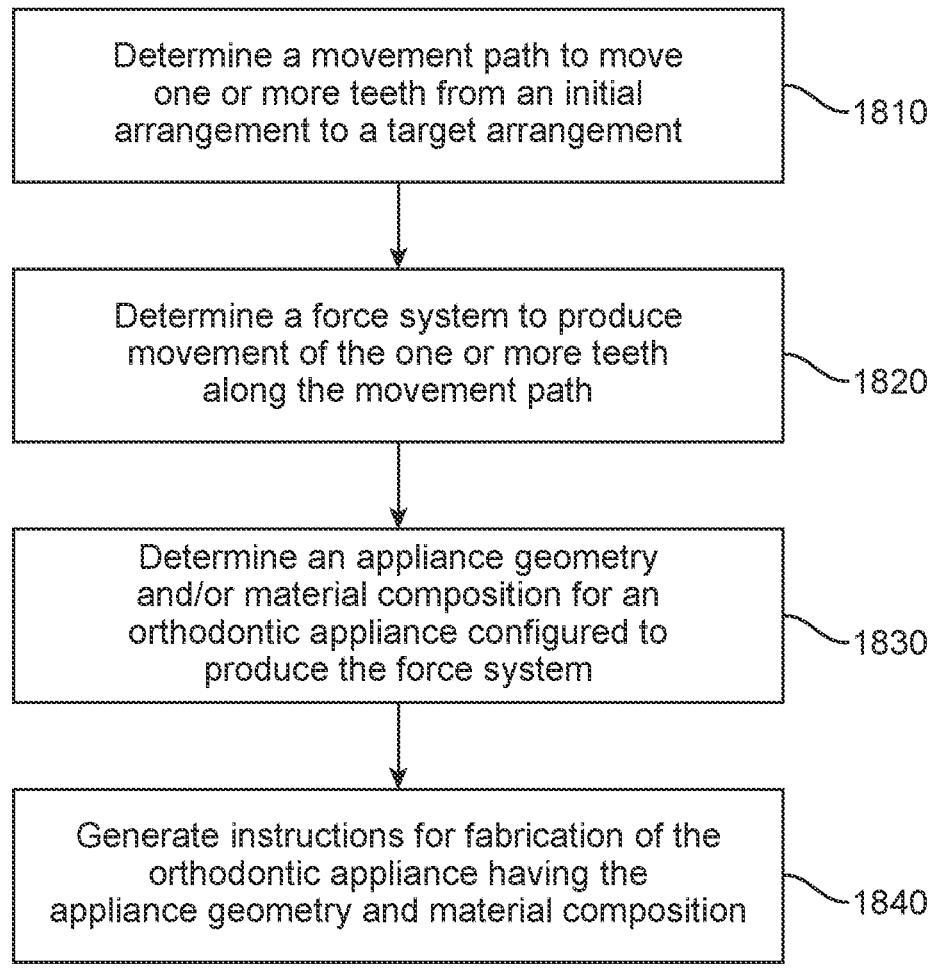
FIG. 17 illustrates a method for designing an orthodontic appliance, in accordance with one or more embodiments herein.

FIG. 17 illustrates a method 1800 for designing an orthodontic appliance to be fabricated, in accordance with embodiments. The method 1800 can be applied to any embodiment of the orthodontic appliances described herein. Some or all of the operations of the method 200 can be performed by any suitable data processing system or device, e.g., one or more processors configured with suitable instructions.

In block 1810, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 1820, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Determination of the force system can be performed in a variety of ways. For example, in some embodiments, the force system is determined on a patient-by-patient basis, e.g., using patient-specific data. Alternatively or in combination, the force system can be determined based on a generalized model of tooth movement (e.g., based on experimentation, modeling, clinical data, etc.), such that patient-specific data is not necessarily used. In some embodiments, determination of a force system involves calculating specific force values to be applied to one or more teeth to produce a particular movement. Alternatively, determination of a force system can be performed at a high level without calculating specific force values for the teeth. For instance, block 1820 can involve determining a particular type of force to be applied (e.g., extrusive force, intrusive force, translational force, rotational force, tipping force, torqueing force, etc.) without calculating the specific magnitude and/or direction of the force.

In block 1830, an appliance geometry and/or material composition for an orthodontic appliance configured to produce the force system is determined. The appliance can be any embodiment of the appliances discussed herein, such as an appliance having variable localized properties, integrally formed components, and/or power arms.

For example, in some embodiments, the appliance comprises a heterogeneous thickness, a heterogeneous stiffness, or a heterogeneous material composition. In some embodiments, the appliance comprises two or more of a heterogeneous thickness, a heterogeneous stiffness, or a heterogeneous material composition. In some embodiments, the appliance comprises a heterogeneous thickness, a heterogeneous stiffness, and a heterogeneous material composition. The heterogeneous thickness, stiffness, and/or material composition can be configured to produce the force system for moving the teeth, e.g., by preferentially applying forces at certain locations on the teeth. For example, an appliance with heterogeneous thickness can include thicker portions that apply more force on the teeth than thinner portions. As another example, an appliance with heterogeneous stiffness can include stiffer portions that apply more force on the teeth than more elastic portions. Variations in stiffness can be achieved by varying the appliance thickness, material composition, and/or degree of photopolymerization, as described herein.

In some embodiments, determining the appliance geometry and/or material composition comprises determining the geometry and/or material composition of one or more integrally formed components to be directly fabricated with an appliance shell. The integrally formed component can be any of the embodiments described herein. The geometry and/or material composition of the integrally formed component(s) can be selected to facilitate application of the force system onto the patient's teeth. The material composition of the integrally formed component can be the same as or different from the material composition of the shell.

In some embodiments, determining the appliance geometry comprises determining the geometry for a variable gable bend.

The block 1830 can involve analyzing the desired force system in order to determine an appliance geometry and material composition that would produce the force system. In some embodiments, the analysis involves determining appliance properties (e.g., stiffness) at one or more locations that would produce a desired force at the one or more locations. The analysis can then involve determining an appliance geometry and material composition at the one or more locations to achieve the specified properties. Determination of the appliance geometry and material composition can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA. For creating finite element models and analyzing them, program products from a number of vendors can be used, including finite element analysis packages from ANSYS, Inc., of Canonsburg, PA, and SIMULIA (Abaqus) software products from Dassault Systèmes of Waltham, MA.

Optionally, one or more appliance geometries and material compositions can be selected for testing or force modeling. As noted above, a desired tooth movement, as well as a force system required or desired for eliciting the desired tooth movement, can be identified. Using the simulation environment, a candidate appliance geometry and composition can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

Optionally, block 1830 can further involve determining the geometry of one or more auxiliary components to be used in combination with the orthodontic appliance in order to exert the force system on the one or more teeth. Such auxiliaries can include one or more of tooth-mounted attachments, elastics, wires, springs, bite blocks, arch expanders, wire-and-bracket appliances, shell appliances, headgear, or any other orthodontic device or system that can be used in conjunction with the orthodontic appliances herein. The use of such auxiliary components may be advantageous in situations where it is difficult for the appliance alone to produce the force system. Additionally, auxiliary components can be added to the orthodontic appliance in order to provide other desired functionalities besides producing the force system, such as mandibular advancement splints to treat sleep apnea, pontics to improve aesthetic appearance, and so on. In some embodiments, the auxiliary components are fabricated and provided separately from the orthodontic appliance. Alternatively, the geometry of the orthodontic appliance can be modified to include one or more auxiliary components as integrally formed components.

In block 1840, instructions for fabrication of the orthodontic appliance having the appliance geometry and material composition are generated. The instructions can be configured to control a fabrication system or device in order to produce the orthodontic appliance with the specified appliance geometry and material composition. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.). Optionally, the instructions can be configured to cause a fabrication machine to directly fabricate the orthodontic appliance with teeth receiving cavities having variable gable bends, as discussed above and herein. In alternative embodiments, the instructions can be configured for indirect fabrication of the appliance, e.g., by thermoforming.

Although the above blocks show a method 1800 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 200 may be performed with any suitable fabrication system or device, such as the embodiments described herein. Some of the blocks may be optional, and the order of the blocks can be varied as desired. For instance, in some embodiments, block 1820 is optional, such that block 1830 involves determining the appliance geometry and/or material composition based directly on the tooth movement path rather than based on the force system.

Figure 18:
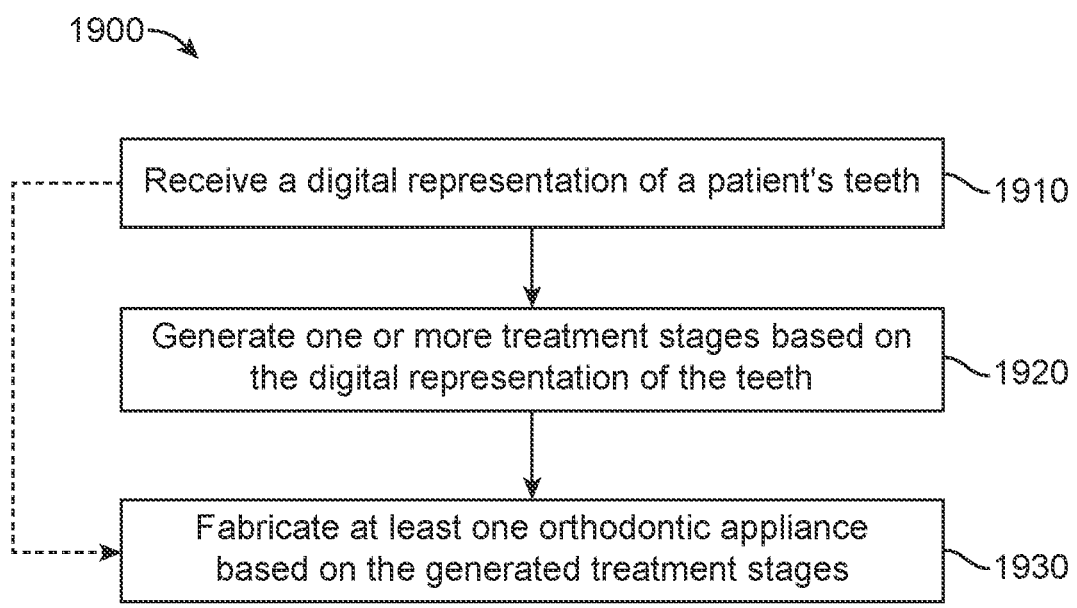
FIG. 18 illustrates a method for planning an orthodontic treatment, in accordance with one or more embodiments herein.

FIG. 18 illustrates a method 1900 for digitally planning an orthodontic treatment and/or design or fabrication of an appliance, in accordance with embodiments. The method 1900 can be applied to any of the treatment procedures described herein and can be performed by any suitable data processing system.

In block 1910, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 1920, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 1930, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 18, design and/or fabrication of an orthodontic appliance, and perhaps a particular orthodontic treatment, may include use of a representation of the patient's teeth (e.g., receive a digital representation of the patient's teeth 1910), followed by design and/or fabrication of an orthodontic appliance based on a representation of the patient's teeth in the arrangement represented by the received representation.

Optionally, some or all of the blocks of the method 1900 are performed locally at the site where the patient is being treated and during a single patient visit, referred to herein as "chair side manufacturing." Chair side manufacturing can involve, for example, scanning the patient's teeth, automatically generating a treatment plan with treatment stages, and immediately fabricating one or more orthodontic appliance(s) to treat the patient using a chair side direct fabrication machine, all at the treating professional's office during a single appointment. In embodiments where a series of appliances are used to treat the patient, the first appliance may be produced chair side for immediate delivery to the patient, with the remaining appliances produced separately (e.g., off site at a lab or central manufacturing facility) and delivered at a later time (e.g., at a follow up appointment, mailed to the patient). Alternatively, the methods herein can accommodate production and immediate delivery of the entire series of appliances on site during a single visit. Chair side manufacturing can thus improve the convenience and speed of the treatment procedure by allowing the patient to immediately begin treatment at the practitioner's office, rather than having to wait for fabrication and delivery of the appliances at a later date. Additionally, chair side manufacturing can provide improved flexibility and efficiency of orthodontic treatment. For instance, in some embodiments, the patient is re-scanned at each appointment to determine the actual positions of the teeth, and the treatment plan is updated accordingly. Subsequently, new appliances can be immediately produced and delivered chair side to accommodate any changes to or deviations from the treatment plan.

Figure 19:
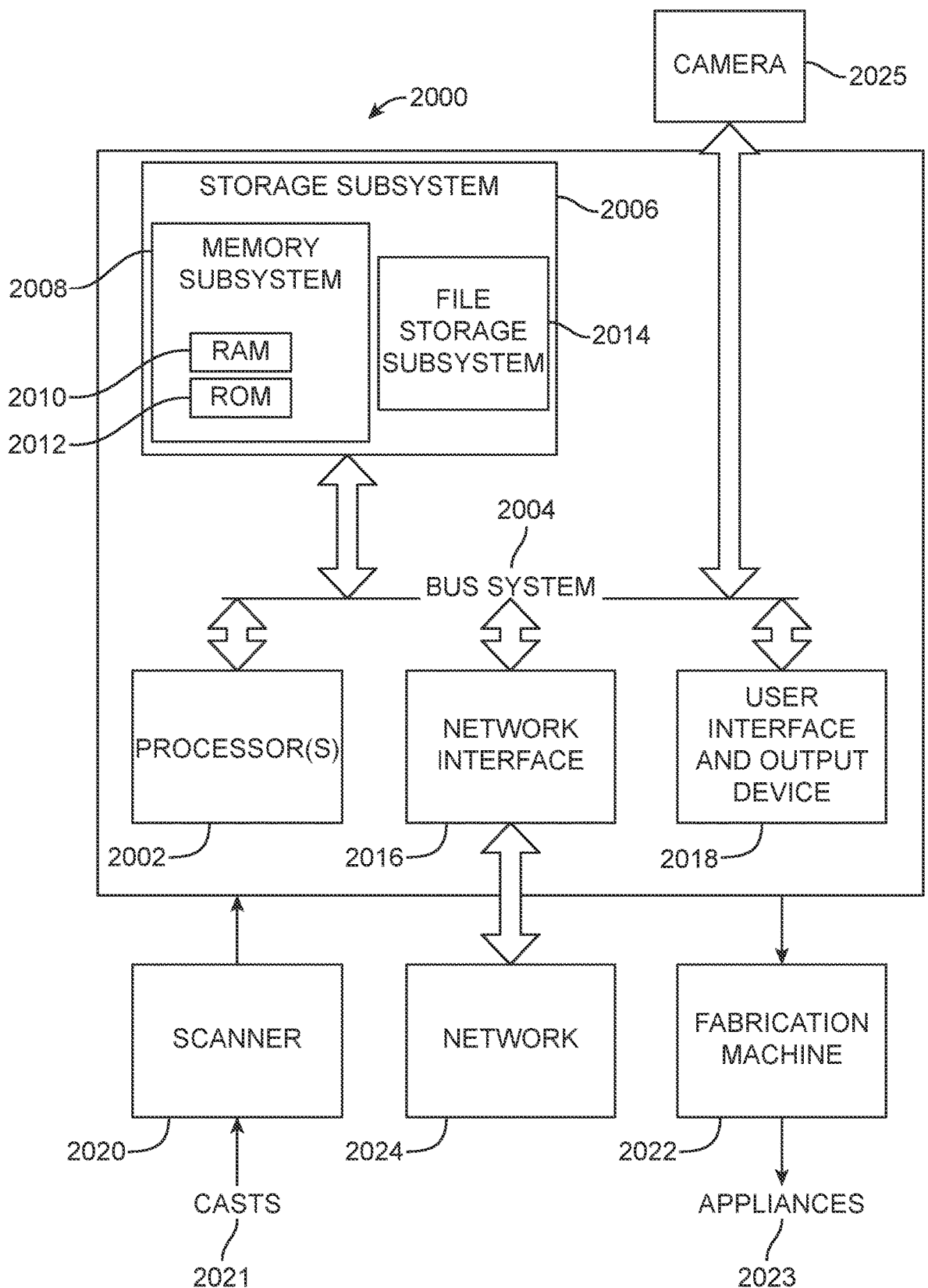
FIG. 19 is a simplified block diagram of a system for designing an orthodontic appliance and planning an orthodontic treatment, in accordance with one or more embodiments herein.

FIG. 19 is a simplified block diagram of a data processing system 2000 that may be used in executing methods and processes described herein. The data processing system 2000 typically includes at least one processor 2002 that communicates with one or more peripheral devices via bus subsystem 2004. These peripheral devices typically include a storage subsystem 2006 (memory subsystem 2008 and file storage subsystem 2014), a set of user interface input and output devices 2018, and an interface to outside networks 2016. This interface is shown schematically as "Network Interface" block 2016, and is coupled to corresponding interface devices in other data processing systems via communication network interface 2024. Data processing system 2000 can include, for example, one or more computers, such as a personal computer, workstation, mainframe, laptop, and the like.

The user interface input devices 2018 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 2006 maintains the basic required programming, including computer readable media having instructions (e.g., operating instructions, etc.), and data constructs. The program modules discussed herein are typically stored in storage subsystem 2006. Storage subsystem 2006 typically includes memory subsystem 2008 and file storage subsystem 2014. Memory subsystem 2008 typically includes a number of memories (e.g., RAM 2010, ROM 2012, etc.) including computer readable memory for storage of fixed instructions, instructions and data during program execution, basic input/output system, etc. File storage subsystem 2014 provides persistent (non-volatile) storage for program and data files, and can include one or more removable or fixed drives or media, hard disk, floppy disk, CD-ROM, DVD, optical drives, and the like. One or more of the storage systems, drives, etc., may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 2020 includes any means for obtaining a digital representation (e.g., images, surface topography data, etc.) of a patient's teeth (e.g., by scanning physical models of the teeth such as casts 2027, by scanning impressions taken of the teeth, or by directly scanning the intraoral cavity), which can be obtained either from the patient or from treating professional, such as an orthodontist, and includes means of providing the digital representation to data processing system 2000 for further processing. Scanner 2020 may be located at a location remote with respect to other components of the system and can communicate image data and/or information to data processing system 2000, for example, via a network interface 2024. Fabrication machine 2022 fabricates appliances 2023 based on a treatment plan, including data set information received from data processing system 2000. Fabrication machine 2022 can, for example, be located at a remote location and receive data set information from data processing system 2000 via network interface 2024. The camera 2025 may include any image capture device configured to capture still images or movies. The camera 2025 may facilitate capturing various perspectives of a patient's dentition. In some implementations, the camera 2025 may facilitate capture of images at various focal lengths and distances from the patient.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing blocks can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein.

As used herein the terms "dental appliance," and "tooth receiving appliance" are treated synonymously. As used herein, a "dental positioning appliance" or an "orthodontic appliance" may be treated synonymously, and may include any dental appliance configured to change the position of a patient's teeth in accordance with a plan, such as an orthodontic treatment plan. A "patient," as used herein may include any person, including a person seeking dental/orthodontic treatment, a person undergoing dental/orthodontic treatment, and a person who has previously undergone dental/orthodontic treatment. A "patient" may include a customer or a prospective customer of orthodontic treatment, such as a person who is using the visualization tools herein to inform a decision to undergo orthodontic treatment at all or a decision to select a specific orthodontic treatment plan. A "dental positioning appliance" or "orthodontic appliance," as used herein, may include a set of dental appliances configured to incrementally change the position of a patient's teeth over time. As noted herein, dental positioning appliances and/or orthodontic appliances may comprise polymeric appliances configured to move a patient's teeth in accordance with an orthodontic treatment plan.

As used herein the term "and/or" may be used as a functional word to indicate that two words or expressions are to be taken together or individually. For example, the phrase "A and/or B" encompasses A alone, B alone, and A and B together. Depending on context, the term "or" need not exclude one of a plurality of words/expressions. As an example, the phrase "A or B" need not exclude A and B together.

As used herein the terms "torque" and "moment" are treated synonymously.

As used herein a "moment" may encompass a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example. Any discussion herein referring to application of forces on a patient's teeth is equally applicable to application of moments on the teeth, and vice-versa.

As used herein a "plurality of teeth" may encompass two or more teeth. A plurality of teeth may, but need not, comprise adjacent teeth. In some embodiments, one or more posterior teeth comprises one or more of a molar, a premolar, or a canine, and one or more anterior teeth comprising one or more of a central incisor, a lateral incisor, a cuspid, a first bicuspid, or a second bicuspid.

The embodiments disclosed herein may be well suited for moving one or more teeth of the first group of one or more teeth or moving one or more of the second group of one or more teeth, and combinations thereof.

The embodiments disclosed herein may be well suited for combination with one or more commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

Repositioning of teeth may be accomplished with the use of a series of removable elastic positioning appliances such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration. Repositioning of teeth may be accomplished through other series of removable orthodontic and/or dental appliances, including polymeric shell appliances.

A computer system, as used in this paper, is intended to be construed broadly. In general, a computer system will include a processor, memory, non-volatile storage, and an interface. A typical computer system will usually include at least a processor, memory, and a device (e.g., a bus) coupling the memory to the processor. The processor can be, for example, a general-purpose central processing unit (CPU) such as a microprocessor, or a special-purpose processor, such as a microcontroller.

The memory can include, by way of example but not limitation, random access memory (RAM), such as dynamic RANI (DRAM) and static RAM (SRAM). The memory can be local, remote, or distributed. The bus can also couple the processor to non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software on the computer system. The non-volatile storage can be local, remote, or distributed. The non-volatile storage is optional because systems can be created with all applicable data available in memory.

Software is typically stored in the non-volatile storage. Indeed, for large programs, it may not even be possible to store the entire program in the memory. Nevertheless, it should be understood that for software to run, if necessary, it is moved to a computer-readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at an applicable known or convenient location (from non-volatile storage to hardware registers) when the software program is referred to as "implemented in a computer-readable storage medium." A processor is considered to be "configured to execute a program" when at least one value associated with the program is stored in a register readable by the processor.

In one example of operation, a computer system can be controlled by operating system software, which is a software program that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus can also couple the processor to the interface. The interface can include one or more input and/or output (I/O) devices. Depending upon implementation-specific or other considerations, the I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device. The interface can include one or more of a modem or network interface. It will be appreciated that a modem or network interface can be considered to be part of the computer system. The interface can include an analog modem, ISDN modem, cable modem, token ring interface, satellite transmission interface (e.g. "direct PC"), or other interfaces for coupling a computer system to other computer systems. Interfaces enable computer systems and other devices to be coupled together in a network.

The computer systems can be compatible with or implemented as part of or through a cloud-based computing system. As used in this paper, a cloud-based computing system is a system that provides virtualized computing resources, software and/or information to end user devices. The computing resources, software and/or information can be virtualized by maintaining centralized services and resources that the edge devices can access over a communication interface, such as a network. "Cloud" may be a marketing term and for the purposes of this paper can include any of the networks described herein. The cloud-based computing system can involve a subscription for services or use a utility pricing model. Users can access the protocols of the cloud-based computing system through a web browser or other container application located on their end user device.

A computer system can be implemented as an engine, as part of an engine or through multiple engines. As used in this paper, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the FIGS. in this paper.

The engines described in this paper, or the engines through which the systems and devices described in this paper can be implemented, can be cloud-based engines. As used in this paper, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud based datastore is a datastore that is compatible with cloud-based computing systems and engines.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining. Additionally, though reference is made herein to orthodontic appliances, at least some of the techniques described herein may apply to restorative and/or other dental appliances, including without limitation crowns, veneers, teeth-whitening appliances, teeth-protective appliances, etc.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method of rendering a patient's gingiva, the computer-implemented method comprising:
    capturing a first 2D image of a patient's face, including their teeth and gingiva;
    building a parametric model of the patient's gingiva based on the first 2D image, wherein the parametric model comprises patient-specific input parameters of the patient's gingiva;
    aligning coordinates of the patient-specific parameters of the patient's gingiva; and
    rendering a second 2D image of the patient's face with teeth and gingiva based on the aligned coordinates of the patient's gingiva.

2. The computer-implemented method of claim 1, wherein building the parametric model of the patient's gingiva comprises:
    finding edges of teeth, gingiva and lips in the first 2D image; and
    determining the patient-specific input parameters from the edges of the teeth, the lips, and the gingiva.

3. The computer-implemented method of claim 1, wherein building the parametric model of the patient's gingiva further comprises modifying the patient-specific input parameters based on simulated input parameters, wherein one or more of the simulated input parameters are based on the parametric model of the patient's teeth.

4. The computer-implemented method of claim 3, wherein the simulated input parameters comprise one or more of: a gingiva tip parameter, an ideal tooth height, a tooth thickness, a distance from a gingiva line to a lip, or a visible tooth height.

5. The computer-implemented method of claim 3, wherein building the parametric model of the patient's gingiva comprises:
    modeling the parametric model of the patient's teeth as a cylinder;
    identifying coordinates on the cylinder defined by simulated input parameters comprising, a gingiva tip parameter, a visible tooth height, and a distance from a gingiva line to the lip;
    cutting the cylinder cross-sectionally by a tilted plane; and
    simulating a parameterized gingiva line as the line of intersection between the tilted plane and the cylinder.

6. The computer-implemented method of claim 1, wherein the patient-specific input parameters comprise one or more of: a maximal distance between a lip and a gingiva line, a minimal distance between the lip and the gingiva line, or a width of a tooth at an incisal edge.

7. The computer-implemented method of claim 1, wherein the coordinates of the parametric model of the patient's gingiva are aligned to a second degree polynomial.

8. The computer-implemented method of claim 1, further comprising building a parametric 3D model of the patient's teeth based on the first 2D image, using one or more case-specific parameters for one or more shapes associated with at least one of the patient's teeth.

9. The computer-implemented method of claim 8, further comprising:
- finding edges of teeth, gingiva, and lips in the first 2D image; and
- aligning the parametric 3D tooth model to the edges of the teeth, the gingiva, and the lips in the first 2D image.

10. The computer-implemented method of claim 1, wherein the first 2D image comprises a profile image representing a profile of the patient's face.

11. A non-transitory computer readable medium that includes instructions that, when executed by a processor, cause the processor to perform a method, the method comprising:
- capturing a first 2D image of a patient's face, including their teeth and gingiva;
- building a parametric model of the patient's gingiva based on the first 2D image, wherein the parametric model comprises patient-specific input parameters of the patient's gingiva;
- aligning coordinates of the patient-specific parameters of the patient's gingiva; and
- rendering a second 2D image of the patient's face with teeth and gingiva based on the aligned coordinates of the patient's gingiva.

12. The non-transitory computer readable medium of claim 11, wherein building the parametric model of the patient's gingiva comprises:
- finding edges of teeth, gingiva and lips in the first 2D image; and
- determining the patient-specific input parameters from the edges of the teeth, the lips, and the gingiva.

13. The non-transitory computer readable medium of claim 11, wherein building the parametric model of the patient's gingiva further comprises modifying the patient-specific input parameters based on simulated input parameters, wherein one or more of the simulated input parameters are based on the parametric model of the patient's teeth.

14. The non-transitory computer readable medium of claim 13, wherein the simulated input parameters comprise one or more of: a gingiva tip parameter, an ideal tooth height, a tooth thickness, a distance from a gingiva line to a lip, or a visible tooth height.

15. The non-transitory computer readable medium of claim 11, wherein the patient-specific input parameters comprise one or more of: a maximal distance between a lip and a gingiva line, a minimal distance between the lip and the gingiva line, or a width of a tooth at an incisal edge.

16. The non-transitory computer readable medium of claim 11, wherein building the parametric model of the patient's gingiva comprises:
- modeling the parametric model of the patient's teeth as a cylinder;
- identifying coordinates on the cylinder defined by simulated input parameters comprising, a gingiva tip parameter, a visible tooth height, and a distance from a gingiva line to the lip;
- cutting the cylinder cross-sectionally by a tilted plane; and
- simulating a parameterized gingiva line as the line of intersection between the tilted plane and the cylinder.

17. A system comprising:
- a photo parameterization engine configured to generate a parameterized gingiva line and a 3D parametric arch model from a 2D image of a patient's face, gingiva, and teeth, the 3D parametric arch model including case-specific parameters for a shape of at least one of the patient's teeth, the parameterized gingiva line including patient-specific input parameters for a shape of the gingiva;
- a parametric treatment prediction engine configured to simulate orthodontic treatment of a patient based on the 3D parametric arch model and historic models of a plurality of patients; and
- a treatment projection rendering engine configured to render the 3D parametric arch model,
- wherein the photo parameterization engine, the parametric treatment prediction engine, and the treatment projection rendering engine are together configured to perform a method, method comprising:
  - capturing a first 2D image of the patient's face, including their teeth and gingiva;
  - aligning coordinates of patient-specific parameters of the patient's gingiva; and
  - rendering a second 2D image of the patient's face with teeth and gingiva based on the aligned coordinates of the patient's gingiva.

18. The system of claim 17, wherein the method further comprises building a parametric model of the patient's gingiva based on the first 2D image, the parametric model comprising patient-specific input parameters for the patient's gingiva.

* * * * *